United States Patent
Platt

(10) Patent No.: US 7,954,175 B2
(45) Date of Patent: Jun. 7, 2011

(54) STRUCTURE AND METHOD FOR STABILIZING AN ARCHER'S HAND

(76) Inventor: David C. Platt, Morrison, CO (US)

( * ) Notice: Subject to any disclaimer, the term of this patent is extended or adjusted under 35 U.S.C. 154(b) by 884 days.

(21) Appl. No.: 11/933,330

(22) Filed: Oct. 31, 2007

(65) Prior Publication Data

US 2008/0183116 A1 Jul. 31, 2008

Related U.S. Application Data

(60) Provisional application No. 60/887,067, filed on Jan. 29, 2007.

(51) Int. Cl.
*A63B 71/14* (2006.01)

(52) U.S. Cl. .......... 2/161.5; 2/159; 2/160; 2/161.1; 2/161.2; 124/5; 124/23.1; 124/86; 124/88; 602/21

(58) Field of Classification Search .......... 124/5, 23.1, 124/86, 88; 2/159, 160, 161.1, 161.2, 161.5; 602/21
See application file for complete search history.

(56) References Cited

U.S. PATENT DOCUMENTS

| | | | | | |
|---|---|---|---|---|---|
| 3,218,089 | A | * | 11/1965 | Marchand | 280/822 |
| 3,368,811 | A | * | 2/1968 | Finney | 473/300 |
| 3,572,312 | A | * | 3/1971 | Foster | 124/23.1 |
| 3,815,908 | A | * | 6/1974 | Hashimoto | 473/62 |
| 4,138,108 | A | * | 2/1979 | Robinson | 473/62 |
| 4,502,688 | A | * | 3/1985 | Papp | 473/213 |
| 4,653,121 | A | * | 3/1987 | Kassal et al. | 2/160 |
| 4,665,565 | A | * | 5/1987 | Odom | 2/161.2 |
| 4,691,387 | A | * | 9/1987 | Lopez | 2/161.3 |
| 4,714,071 | A | * | 12/1987 | Saunders | 124/88 |
| 4,777,666 | A | * | 10/1988 | Beverlin | 2/161.5 |
| 4,836,177 | A | * | 6/1989 | Williams | 124/89 |
| 4,894,866 | A | * | 1/1990 | Walker | 2/161.6 |
| 5,009,216 | A | * | 4/1991 | Ross | 124/88 |
| 5,070,856 | A | * | 12/1991 | Plummer | 124/88 |
| 5,110,154 | A | * | 5/1992 | Street | 280/822 |
| 5,123,674 | A | * | 6/1992 | Bagneres et al. | 280/821 |
| 5,267,943 | A | * | 12/1993 | Dancyger | 602/5 |
| 5,277,170 | A | * | 1/1994 | Carella | 124/86 |
| 5,312,134 | A | * | 5/1994 | Goode et al. | 280/822 |
| 5,323,754 | A | * | 6/1994 | Pittman et al. | 124/35.2 |
| 5,328,205 | A | * | 7/1994 | Bacharach | 280/822 |
| 5,445,566 | A | * | 8/1995 | Hayes | 473/62 |
| 5,484,392 | A | * | 1/1996 | Sydor et al. | 602/5 |
| 5,513,657 | A | * | 5/1996 | Nelson | 128/879 |
| 5,516,150 | A | * | 5/1996 | Goode et al. | 280/821 |
| 5,531,211 | A | * | 7/1996 | Wilfong, Jr. | 124/86 |
| 5,592,694 | A | * | 1/1997 | Yewer, Jr. | 2/161.1 |
| 5,617,838 | A | * | 4/1997 | Peruski | 124/88 |

(Continued)

*Primary Examiner* — Gene Kim
*Assistant Examiner* — Alexander R Niconovich
(74) *Attorney, Agent, or Firm* — Roger A. Jackson

(57) ABSTRACT

An archer's hand support structure apparatus and method of use is disclosed to help stabilize an archer's hand during string draw and string release of an archer's bow. The archer's hand support structure apparatus includes a band of flexible material adapted to encase the archer's hand, the band having a first edge portion extending adjacent to an archer's distal hand portion and a second edge portion extending adjacent to an archer's proximal hand portion. The band also includes an aperture therethrough disposed substantially adjacent to the first edge portion for receiving a thumb of the archer's hand. Further included is a stiffener positioned adjacent to the band, the stiffener also extending lengthwise substantially from the band first edge portion to the band second edge portion and the band also includes structure for removably engaging the band from the archer's bow.

3 Claims, 20 Drawing Sheets

U.S. PATENT DOCUMENTS

| | | | | |
|---|---|---|---|---|
| 5,810,753 A * | 9/1998 | Eberbach | | 602/21 |
| 5,853,000 A * | 12/1998 | Torgerson et al. | | 124/88 |
| 5,853,001 A * | 12/1998 | Vyprachticky | | 124/88 |
| 5,887,282 A * | 3/1999 | Lenhart | | 2/159 |
| 5,988,681 A * | 11/1999 | Vesalainen et al. | | 280/821 |
| 6,173,707 B1 * | 1/2001 | Howell et al. | | 124/88 |
| 6,199,208 B1 * | 3/2001 | Torbett | | 2/16 |
| 6,233,743 B1 * | 5/2001 | Cummins | | 2/160 |
| 6,386,588 B1 * | 5/2002 | Young et al. | | 280/821 |
| 6,460,891 B1 * | 10/2002 | Jones | | 280/821 |
| 6,536,050 B1 * | 3/2003 | Hill | | 2/161.6 |
| 6,637,773 B1 * | 10/2003 | Trinen et al. | | 280/821 |
| 6,716,185 B1 * | 4/2004 | Rieger | | 602/21 |
| 6,755,440 B1 * | 6/2004 | Jones | | 280/822 |
| 6,827,653 B2 * | 12/2004 | Be | | 473/62 |
| 6,898,804 B2 * | 5/2005 | Sandler | | 2/161.1 |
| 6,942,632 B2 * | 9/2005 | Cho | | 602/64 |
| 7,124,536 B2 * | 10/2006 | Harkey | | 43/21.2 |
| 7,284,546 B2 * | 10/2007 | Maki et al. | | 124/35.2 |
| 7,422,008 B1 * | 9/2008 | Tentler et al. | | 124/35.2 |
| 7,620,999 B2 * | 11/2009 | Winningham | | 2/163 |
| 7,638,699 B2 * | 12/2009 | Buettgen | | 84/387 A |
| 7,770,931 B2 * | 8/2010 | Lenhart | | 280/821 |
| 2003/0070669 A1 * | 4/2003 | Beville | | 124/88 |
| 2006/0174395 A1 * | 8/2006 | Mayo | | 2/160 |
| 2007/0022512 A1 * | 2/2007 | Coulter et al. | | 2/161.1 |
| 2009/0293702 A1 * | 12/2009 | Buettgen | | 84/387 A |

* cited by examiner

STRUCTURE AND METHOD FOR STABILIZING AN ARCHER'S HAND

RELATED PATENT APPLICATION

This application claims priority from U.S. provisional patent application Ser. No. 60/887,067 filed Jan. 29, 2007 by David Platt.

FIELD AND BACKGROUND

The present invention broadly relates to the sport of archery. More particularly, the exemplary embodiments of this invention are directed to assist in stabilizing the hand position of an archer on the handle of a bow while shooting. Thus, the present invention may be used, for example, by an archer when target shooting or hunting. As such, the embodiments of the present invention function to stabilize the bow body relative to the hand or arm of the archer to reduce undesirable movement during bow string draw and release thus resulting in a desirable improvement in bow shooting accuracy.

As it is known, many archery bows have a relatively high draw weight (the rearward string force) required to flex the bow body to its fully drawn position, being done to give the bow's arrow more range distance wise and more piercing force at a further distance. When this occurs, the bow body undergoes various torques or moments that are particularly present at the location of the archer's hand that is, at the handle or grip of the bow as being the quasi pivotal support point for the bow to react through, both during pull back and release of the bow string. For example, some of these moments tend to rotate the bow handle toward the palm side of the archer's hand about a vertical axis. Other moments tend to tip the upper bow limb toward the archer about a horizontal axis. Each or the combination of these moments may affect the flight accuracy of the arrow and therefore the accuracy of that archer. Moreover, they can strain or fatigue the bow holding hand or have the archer compensating for the previously described moments by attempting to manually create opposing moments in the hand, wrist, or forearm that can further add to arrow inaccuracy due to the variable moment compensation levels of the archer.

Various apparatus have been developed in an effort to more accurately compensate for these aforementioned undesirable moments at the bow handle that are recognized in the prior art. For example, various bow to arm, wrist, or hand structural supports have been proposed to attach to the bow in order to partially support the arm, wrist, or hand of the archer as against the aforementioned moments.

In other efforts to reduce the effect of the previously described bow moments, some archers opt to hold the bow handle loosely with the fingers and thumb projecting forwardly of the handle with the bow handle being received in the space between the thumb and index finger. Since the bow handle is not gripped tightly, the also aforementioned manual compensatory moments, sometimes termed the after shoot jerk; to resist the bow induced moments are substantially eliminated by the loose grip from the archer's hand to the bow. However, this type of bow grip is not natural and many archers tend to grip the bow handle very tightly as an instinctual reaction when shooting. As a result, the moment forces are applied to the wrist of the archer which can affect the accuracy of the arrow's flight as previously discussed.

Another problem is encountered by archers when they are stalking the prey; the archer typically carries the bow by its handle. Because the bow is gripped, the hand and fingers of the archer can become unduly fatigued or tired over time from simply carrying the bow for extended periods of time, especially when transversing rough terrain. Since the bow hunting activity typically occurs over a significant interval of time, the hand may cramp or otherwise become excessively tired resulting in the accuracy of the bow hunter being diminished when game is finally sighted. Moreover, when hunting in a cold climate, the hand may be more exposed to the environment and bow gripping ability and feel reduced by carrying of the bow by the hand.

Further as previously stated, this issue has been recognized in the prior art, starting with apparatus that operate to brace a portion of the archer's hand, wrist, or forearm, thus in looking at U.S. Pat. No. 4,836,177 to Williams disclosed is an archery bow wrist brace apparatus that uses a "U" shaped loop of rigid material that has a padded outer surface, wherein the free ends of the "U" affix to the bow handle and the semi-circular portion of the "U" rests against the user's forearm. In Williams, the purpose being to strengthen the user's wrist in resisting the moment at the bow handle from bow string pull and release by transferring a vertical moment and a horizontal moment between the user's wrist and the bow handle to the user's forearm for strength and stability. However, with Williams having the drawback of a higher surface area unit loading on the archer's forearm due to the smaller diameter band that is in the "U" shape, potentially causing forearm fatigue and pain for the archer.

Further in this area in U.S. Pat. No. 5,853,001 to Vyprachticky disclosed in an archery bow handgrip that appears similar to a pistol grip with an open conic portion that is adjacent to the archer's forearm that is operable to brace the wrist and forearm to one another, however, with the drawback of the size bulkiness of the pistol grip and conic portion combination structurally. Further, in this same area of structural braces adjacent to a portion of an archer's hand in U.S. Pat. No. 5,853,000 to Torgerson et al., disclosed is an archer's wrist brace in the shape of an "L" that is pivotally adjustable at the bow handle. In Torgerson et al., the "L" portion short extension braces against the archer's arm for stability and to help prevent the archer's arm from getting in the path of the bow string. Torgerson et al., has the same problem as Williams in that there is a higher surface area unit loading as against the archer's arm from the relatively small diameter brace, again potentially causing forearm fatigue and pain for the archer.

Continuing, in this area in U.S. Pat. No. 5,617,838 to Peruski disclosed is an archery aid that is structured to be a form for configuring an archer's hand in a flat open shape with only the thumb and index finger forming a cupped shape around a portion of the bow handle, this is beneficial in some archer's minds as hard hand gripping of a bow is attributable to reduce aim accuracy when the arrow is released as the closed hard grip of the hand on the bow handle causes a reactive "jerk" due to the changing forces surrounding the bow handle at arrow release. In Peruski this is due to the archer's wrist resisting an upward and lateral moment at bow string drawback, wherein at string release this upward and lateral moment are suddenly reduced wherein the archer's wrist instantly reacts oppositely from the above mentioned preloading moments at bow string drawback, thereby affecting arrow aim accuracy. Even though Peruski is a partial solution to this line of archery accuracy thinking, there is the added drawback of increasing difficulty in holding and carrying the bow during non arrow shooting periods.

Another prior art approach is in using a special glove that is affixed to the archer's hand that has some stiffening and supportive capabilities that assist the archer's hand, wrist, and forearm. Starting with U.S. Pat. No. 5,070,856 to Plummer disclosed is a hand/bow interface that provides a low friction interface between the archer's hand and the bow handle for the purpose of reducing the effect of the aforementioned "jerk" in Peruski above by lessening the effect of archer involuntary wrist and hand movement into the bow, thus reducing arrow inaccuracy from this archer hand and wrist movement. Plummer has the drawback of still allowing the high string pullback upward and lateral moments at the bow handle being resisted by the archer's hand and wrist that can affect initial arrow aim accuracy.

Further, in this area in United States patent application publication number US 2007/0022512 A1 to Coulter et al., disclosed is a glove with stiffeners primarily for weightlifting and adding stiffening in the area of the back of the hand while leaving the finger tips free for dexterity, while not specific to archery, Coulter et al., does teach a hand glove with stiffener elements. Also, in the hand stiffening glove arts in U.S. Pat. No. 4,138,108 to Robinson, disclosed is a wrist stiffening bowlers glove, bracing primarily between the palm and forearm while desirably leaving the fingers and the thumb free for grasping the bowling ball, while helping to prevent forwards or backwards flexing of the wrist, being somewhat similar to Coulter et al., in having specialized stiffening for a particular application.

Also, in looking at United States patent application publication number US 2006/0174395 A1 to Mayo disclosed is a glove with special attachments for helping to hold weights such as dumb bells, wherein a removably engagable interface exists between the glove palm and the dumb bell grasping area, whereas various means for the removable engagement are disclosed. Further in this area, in U.S. Pat. No. 6,755,440 B1 to Jones disclosed is a snow skiing pole handle to ski glove removable engagement used in conjunction with a special skiing pole handle that pivots in relation to the pole portion of the ski pole to lessen the effect of the attachment between the glove and the handle by adding more flexibility to the hand and handle interface, wherein the attachment is a protrusion that is received into a matching concavity. Continuing, in U.S. Pat. No. 6,898,804 B2 to Sandler disclosed is another ski type glove for attachment to a ski pole handle utilizing a hook and loop fastener between the glove palm and the ski pole handle.

Accordingly, there is a need to provide additional structural features to the hand/bow interface for improving the grip of an archer on the handle of a bow that ultimately results in improved arrow accuracy. There is a further need for apparatus in the hand/bow interface that can help stabilize the hand of the archer as against the various previously described moment forces that result during the increasingly heavy string draw and release of the bow. Further, there is a need for apparatus which can easily and effectively allow the archer to carry the bow during intervals of non use with minimal fatigue especially on the archer's hand, wrist, and arm, wherein the present invention is directed to meeting these needs.

SUMMARY

Broadly, the present invention is an archer's hand support structure apparatus to help stabilize an archer's hand during string draw and string release of an archer's bow. The archer's hand support structure apparatus includes a band of flexible material adapted to encase the archer's hand, the band having a first edge portion extending adjacent to an archer's distal hand portion and a second edge portion extending adjacent to an archer's proximal hand portion. The band also includes an aperture therethrough disposed substantially adjacent to the first edge portion for receiving a thumb of the archer's hand. Further included is a stiffener positioned adjacent to the band, the stiffener also extending lengthwise substantially from the band first edge portion to the band second edge portion and the band also includes a means for removably engaging the band from the archer's bow.

REFERENCE ELEMENT NUMBERS IN FIGURES

Figure 1:
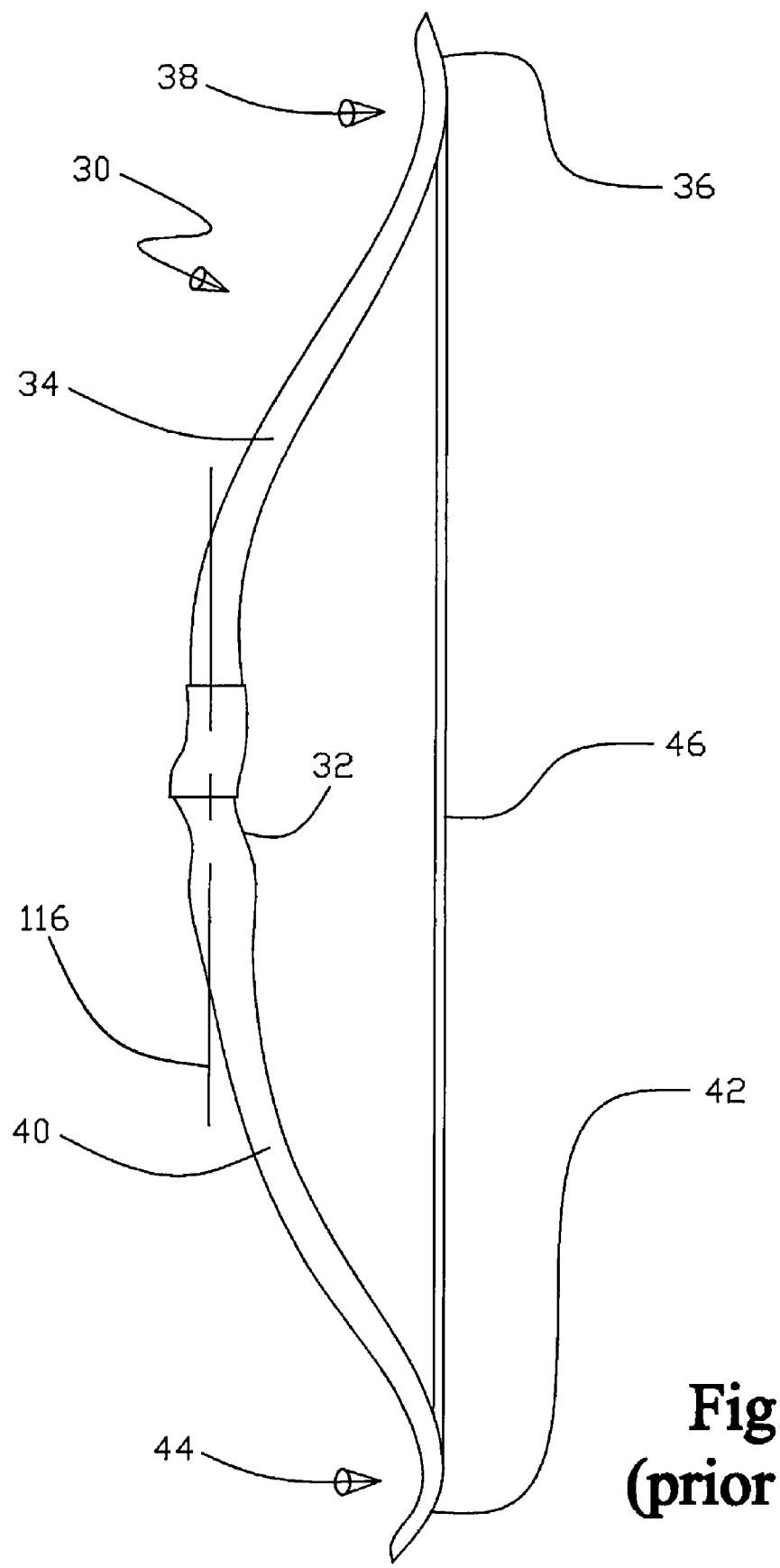
FIG. 1 is a side view and elevation of an exemplary recurve bow according to the prior art.

30 Bow apparatus as embodied in the prior art
32 Grip or handle of bow apparatus 30
34 First limb of bow apparatus 30
36 First tip of bow apparatus 30
38 First recurve of bow apparatus 30
40 Second limb of bow apparatus 30
42 Second tip of bow apparatus 30
44 Second recurve of bow apparatus 30
46 Bow string of bow apparatus 30
50 Compound bow as embodied in the prior art
52 Grip or handle of compound bow 50
54 First rigid arm portion of compound bow 50
56 Second rigid arm portion of compound bow 50
58 First limb of compound bow 50
60 First distal tip of compound bow 50
62 First wheel of compound bow 50
64 Second limb of compound bow 50
66 Second distal tip of compound bow 50
68 Cam of compound bow 50
70 Cable and bowstring combination of compound bow 50
80 Prior art glove of archer
81 Archer
82 Hand of archer
83 Archer's thumb
84 Main body panel of prior art archer glove 80
85 Archer's arm
86 First attachment straps of prior art archer glove 80
88 Gap between straps 86 of prior art archer glove 80
90 Second attachment strap of prior art archer glove 80
92 Side edge of prior art archer glove 80
94 Elongated oval opening of prior art archer glove 80
96 Strip of loop elements of prior art archer glove 80
98 Strip of filaform element mounted on the distal end of strap 86 of prior art archer glove 80
100 Strip of filaform element mounted on the end of distal strap 90 of prior art archer glove 80
102 First rigid support of prior art archer glove 80
104 Pocket of first rigid support 102 of prior art archer glove 80
106 Second rigid support of prior art archer glove 80
108 Pocket of second rigid support 106 of prior art archer glove 80
110 Distal hand portion of archer 81
112 Proximal hand portion of archer 81
114 Lengthwise axis of archer's 81 hand 82
116 Longwise axis of bow 50
118 Higher stiffness direction of stiffener 161
120 Lower stiffness direction of stiffener 161
122 Semi rigid member
124 Palm of archer's 81 hand 82
125 Pocket for member 122
160 Archer's hand support structure apparatus of a first exemplary embodiment 161 Stiffener for archer's hand support structure apparatus of a first 160, second 260, third 310, and fourth 500 exemplary embodiments
162 First fastening elements of archer's glove apparatus 160
163 Pocket of stiffener 161
164 Main body panel band of archer's glove apparatus 160, 260, 310, and 500
166 First edge portion of band 164 of the archer's glove apparatus 160, 260, 310, and 500
167 Second edge portion of band 164 of the archer's glove apparatus 160, 260, 310, and 500
168 Edge of archer's glove apparatus 160
169 Aperture therethrough of archer's glove apparatus 160, 260, 310, and 500
170 Means for removably engaging the band 164 from the archer's 81 bow handle 32 or 52
172 Second fastening element that is cooperative to first fastening element 162 of archer's glove apparatus 160
174 Support base of first fastening element 162
176 Prong of first fastening element 162
177 Central longitudinal axis of first fastening element 162
178 Shaft of prong 176
180 Head of shaft 178
182 Neck of shaft 178
184 Bore for receiving second fastening element 172
186 Female base of second fastening element 172
188 Detent of female base 186
190 Pull rod of female base 186
212 Third fastening element
214 Fourth fastening element
216 Interior of third fastening element 212
218 Lower wall of third fastening element 212
220 Parallel top wall of third fastening element 212
222 Sidewalls of third fastening element 212
224 Elongated oval opening of third fastening element 212
226 Interior of fourth fastening element 214
228 Lower wall of fourth fastening element 214
230 Top wall of fourth fastening element 214
232 Sidewalls of fourth fastening element 214
234 Keyhole shaped opening of fourth fastening element 214
236 Wider region of keyhole opening 234
238 Narrow mouth region of keyhole opening 234
260 Second exemplary embodiment of the archer's hand support structure apparatus
262 Fifth fastening element that is cooperative to third fastening element 212 of archer's glove apparatus 260
264 Sixth fastening element that is cooperative to fourth fastening element 214 of archer's glove apparatus 260
270 Base of fifth fastening element 262
272 Shaft of fifth fastening element 262
274 Elongated oval head of fifth fastening element 262
276 Base of sixth fastening element 264
278 Shaft of sixth fastening element 264
280 Circular head of sixth fastening element 264
282 Nubs of fourth fastening element 214
310 Third exemplary embodiment of the archer's hand support structure apparatus
312 Seventh fastening element
314 Thread of seventh fastening element 312
316 Interior cam surface of seventh fastening element 312
362 Eighth fastening element that is cooperative to seventh fastening element 312
364 Thread that is radially outwardly projecting of the eighth fastening element 362
366 Cam surface of thread 364
400 Draw force of bow 30 or 50
402 Vertical moment arm of bow 30 or 50

404 Vertical moment of bow 30 or 50
410 Horizontal moment arm of bow 30 or 50
412 Horizontal moment of bow 30 or 50
500 Fourth exemplary embodiment of the archer's hand support structure apparatus

DETAILED DESCRIPTION OF THE
EXEMPLARY EMBODIMENTS

The present invention broadly relates to auxiliary aids for archers when shooting an arrow from a bow, for example, when target shooting, hunting, and the like. More specifically, the exemplary embodiments described herein are directed to mechanically linking or nesting the handle or grip of a bow to an archery glove worn by an archer in order to provide a greater stability while shooting an arrow from the bow and while carrying the bow while seeking prey. It should be appreciated that the exemplary embodiments of the present invention are modifications to existing prior art apparatus. As such, these exemplary embodiments may be manufactured as original equipment or, in some instances, retrofitted onto an existing bow handle.

In order to understand the exemplary embodiments of the present invention, it is thus helpful to understand the structure of common types of bows. A first exemplary embodiment of a prior art bow is illustrated in FIG. 1. Here, bow 30 is in the form of a recurve bow and includes a grip or handle 32. A first limb 34 projects upwardly (when in a shooting position) to terminate in a first tip 36. First limb 34 is provided with a first recurve 38, and is known in the art. A second limb 40 projects downwardly (when in a shooting position) from handle 32 to terminate in a second tip 42 with the second limb 40 again being provided with a second recurve 44. A bow string 46 then extends between a first tip 36 and a second tip 42 and is maintained under tension by first and second limbs 34 and 40.

Figure 2:
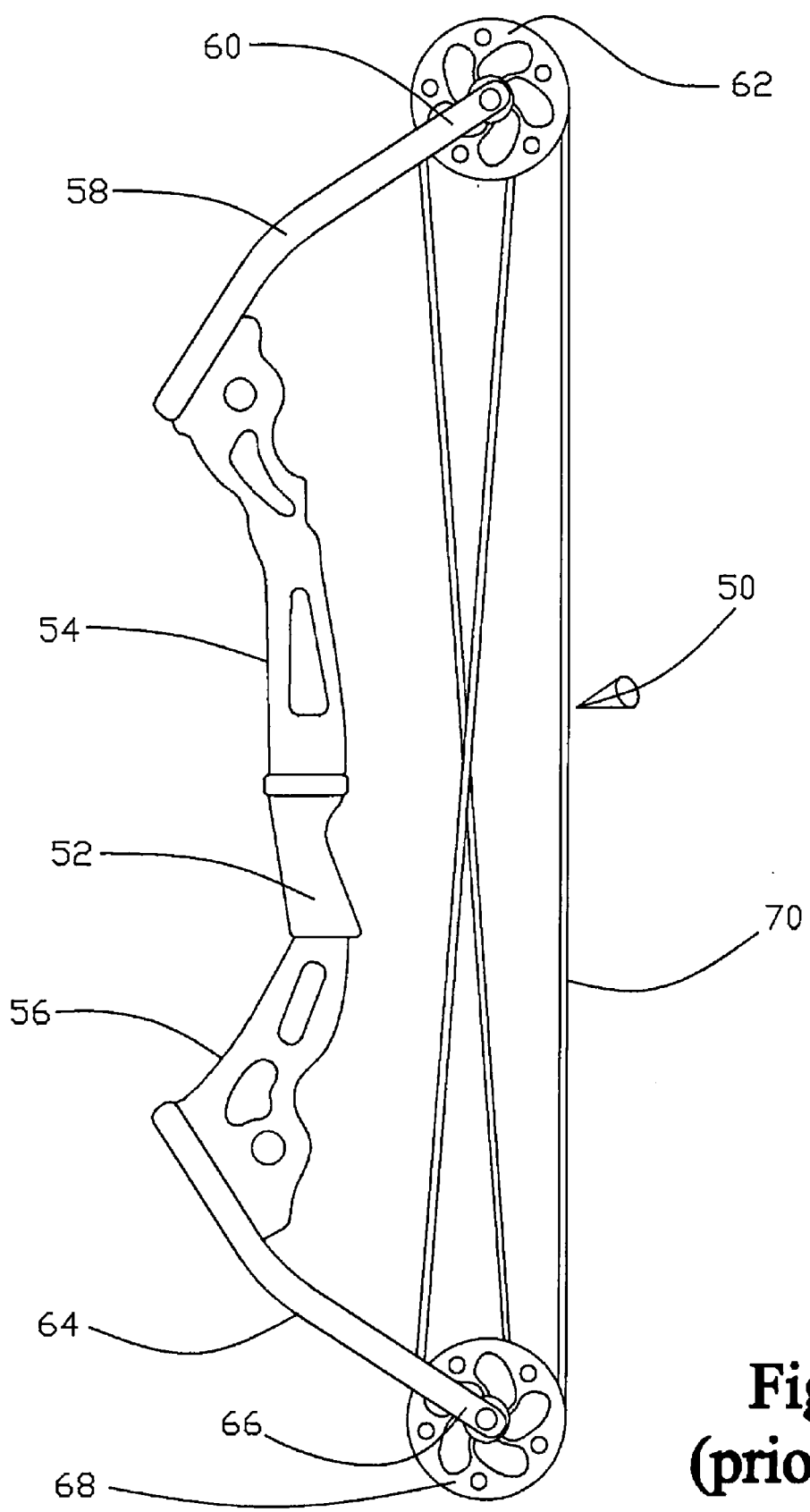
FIG. 2 is a side view and elevation of an exemplary compound bow according to the prior art.

Another type of bow well known in the prior art is known as a "compound bow." An exemplary embodiment of the compound bow 50 is illustrated in FIG. 2. Bow 50 again has a grip or handle 52 from which projects first and second rigid arm portions 54 and 56. A flexible, resilient first limb 58 has its proximal first end secured to the distal end of first arm portion 54 and terminates in a distal first tip 60 that rotatably supports a wheel 62. Similarly, a second limb 64 has its proximal end secured to the distal end of second arm portion 56 and terminates in a distal second tip 66 that rotatably supports a cam 68. Cam 68 and wheel 62 are mechanically linked by a cable and bowstring combination 70.

When using a bow, many archers desire to use an archer's glove that supports the hand and wrist of the archer during shooting activity. An exemplary embodiment of such a prior art archer's glove 80 is introduced in FIG. 3 wherein glove 80 is illustrated in a mounted state on hand 82 of the archer 81. FIGS. 4 and 5 illustrate glove 80 in an opened, flattened state prior to mounting on the hand 82. With respect to these Figures, FIG. 4 illustrates the exterior side of glove 80, when worn, and FIG. 5 illustrates the interior side of glove 80 (when being worn).

Figure 3:
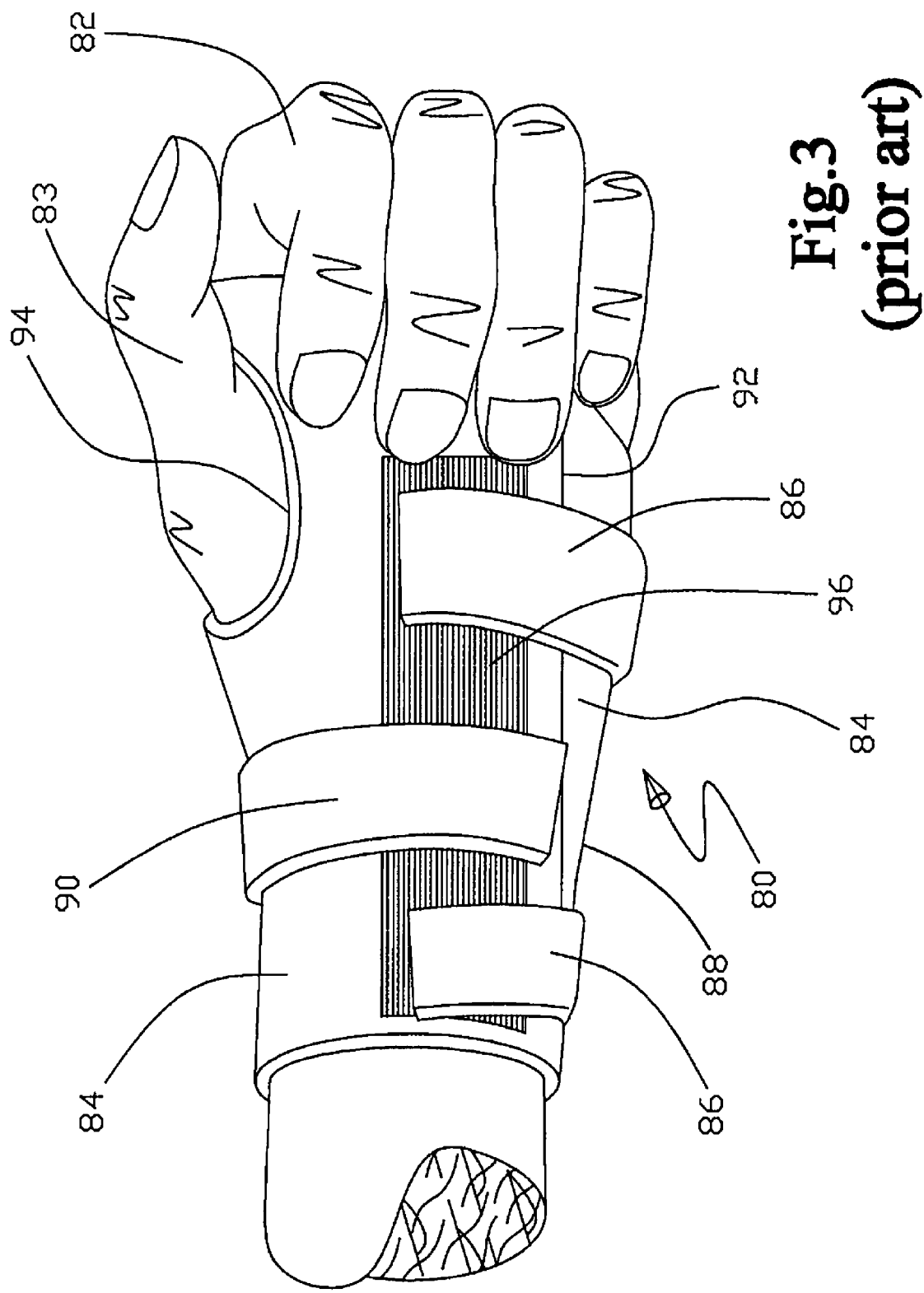
FIG. 3 is a perspective view of an archer's glove apparatus according to an exemplary embodiment of the prior art and in a mounted state on an archer's hand.
Figure 4:
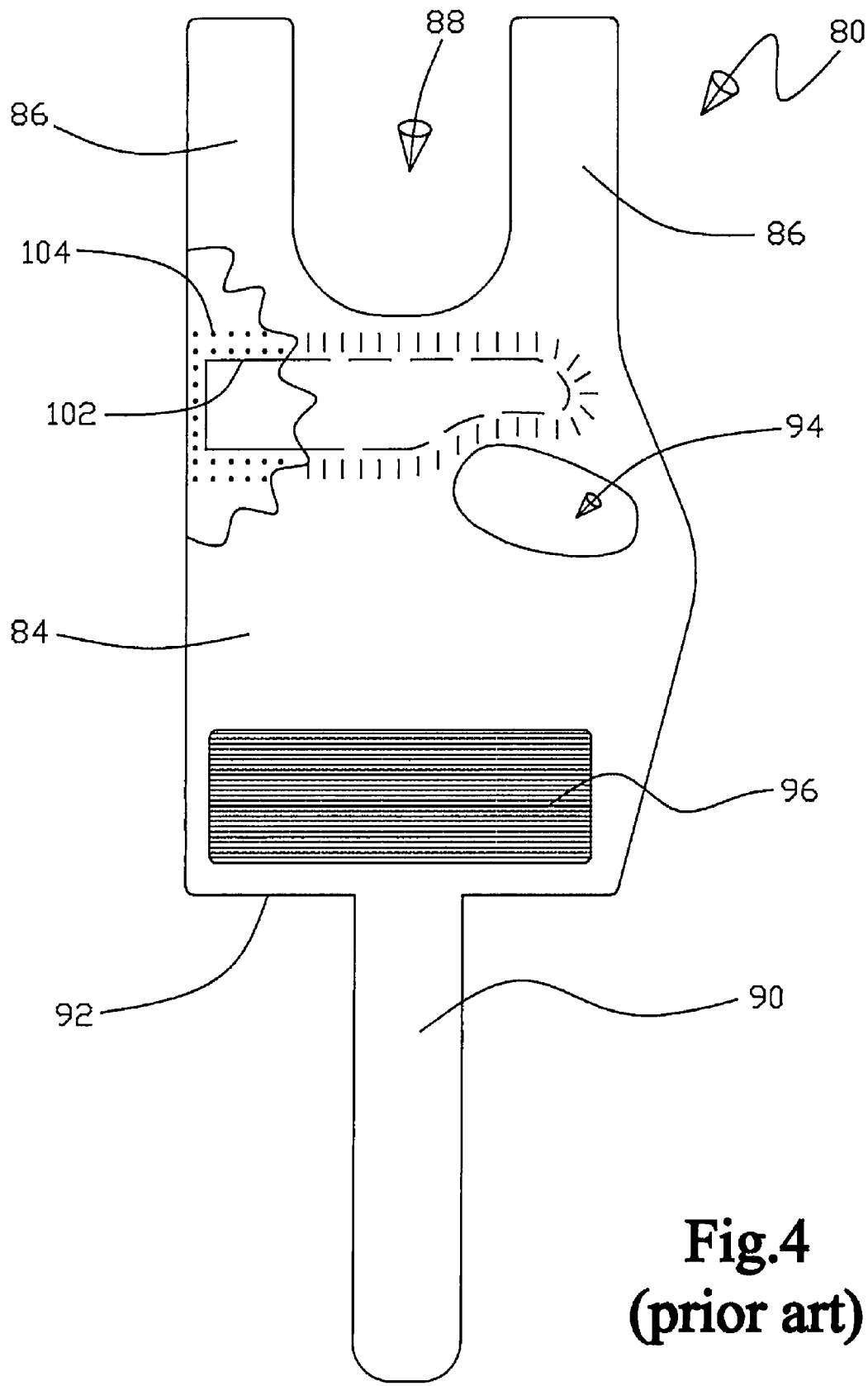
FIG. 4 is a plan view of the archer's glove of FIG. 3 in an open, unwrapped flat state with the glove being viewed from the external side that is worn away from the archers hand.
Figure 5:
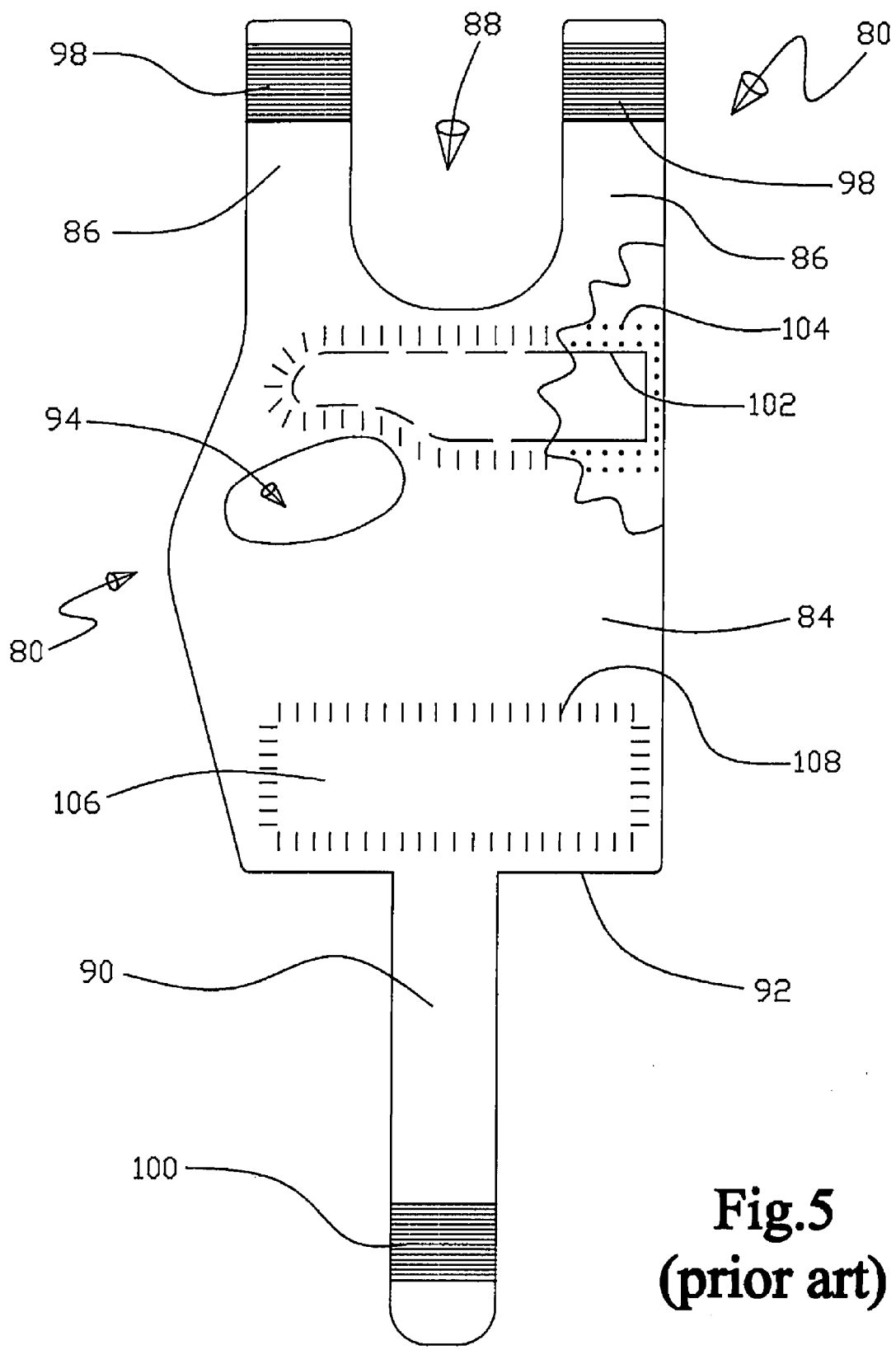
FIG. 5 is a plan view similar to FIG. 4, however, showing the archers glove of FIG. 3 viewed from the inside showing the surface that is against the archers hand when in the mounted state.
Figure 6:
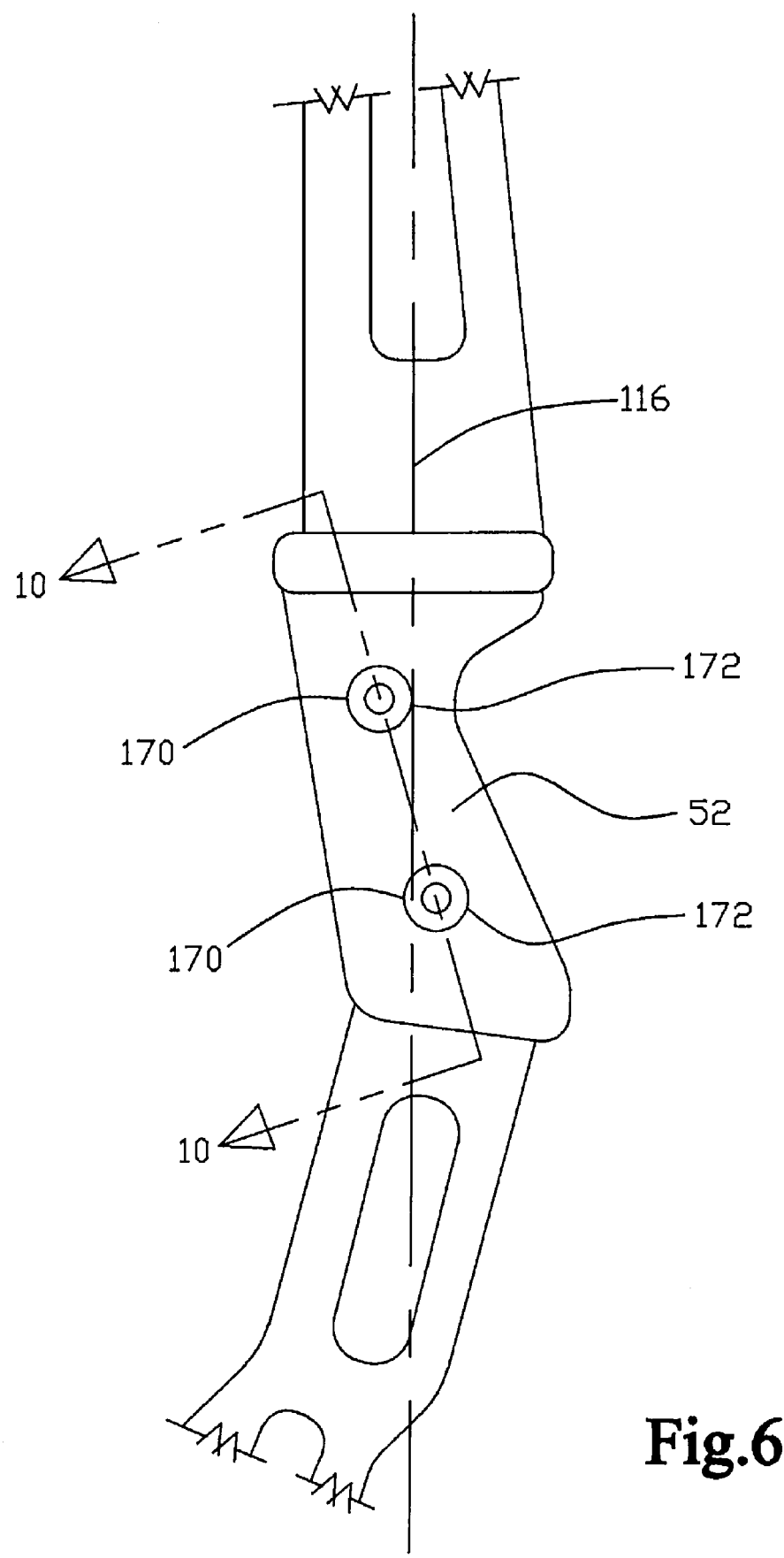
FIG. 6 is a side view in elevation of the handle portion of the compound bow of FIG. 2 illustrating a first exemplary embodiment of the present invention with the second cooperative fastener elements.

With respect to FIGS. 3-5, it may be appreciated that glove 80 includes a main body panel 84 that is adapted to extend around the user's wrist and hand 82. A pair of first attachment straps 86 project on one side of main body panel 84 in a spaced, parallel relation to one another. A gap 88 is therefore formed between straps 86. A second attachment strap 90 projects on an opposite side of main body panel 84 medially of a side edge 92 thereof.

Typically, archer gloves are secured around the hand of the wearer by mating hooking loop fastening members. Thus, as is illustrated in FIG. 4, a strip 96 of loop elements is located proximately to edge 92 and parallel thereto. As is illustrated in FIG. 5, strips 98 of filaform elements are mounted on the distal ends of straps 86 and a strip 100 of filaform elements are mounted on the distal end of attachment strap 90. Thus, when mounted, the pair of straps 86 and attachment strap 90 may wrap around the wrist and hand 82 of the archer 81 with filaform strips 98 and 100 adjustably engaging loop strip 96. As may be seen, the distal end of attachment strap 90 resides in gap 88 when the glove 80 is in a mounted state.

With continued reference to FIGS. 4 and 5, it may seem that an elongated oval opening 94 is formed in main body panel 84 to accommodate the thumb 83 of the archer, as is illustrated in FIG. 3. It may also be appreciated that some archery gloves include rigid support pieces to further stabilize the archer's hand. Thus as is shown in phantom in these figures, a first rigid support 102 is sewn into a pocket 104 and a second rigid support 106 may be sewn into pocket 108 into main body panel 84 parallel to edge 92. For example, rigid support 106 may be generally congruent with filaform strip 96.

With the above structures in mind, the exemplary embodiments of the present invention may be better understood. Broadly, the present invention includes cooperative fasteners that are respectively positioned on the handle of the bow and on the archer's glove, in order to mechanically and releasably interconnect the glove and the handle during use. These cooperative fasteners may be retrofitted onto an existing bow and/or archer's glove or may be manufactured as original equipment. Moreover, it may be possible to manufacture the archer's glove as original equipment containing the cooperative fasteners while retrofitting a bow handle.

Figure 7:
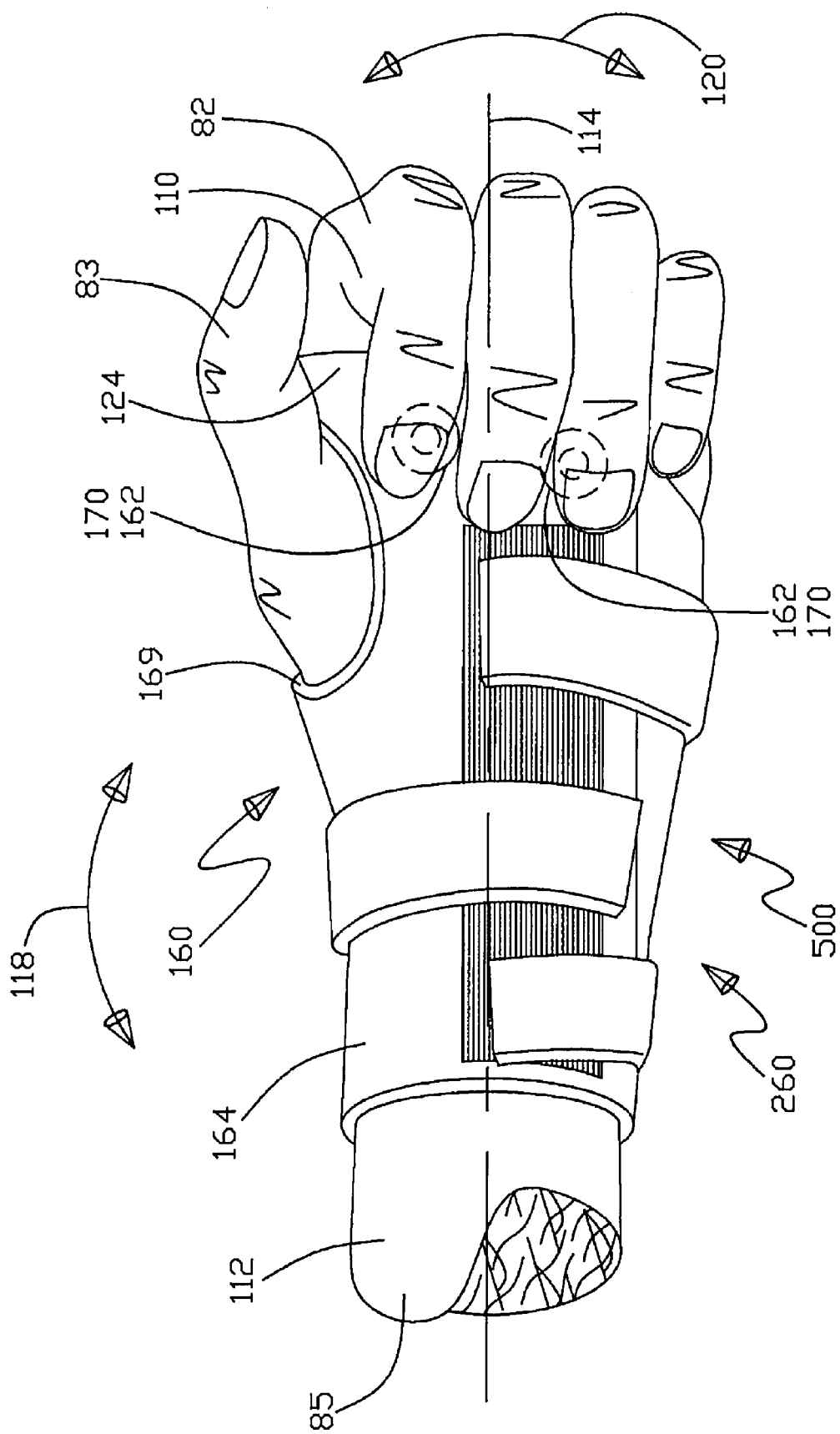
FIG. 7 is a perspective view of the archer's hand and glove, similar to FIG. 3, illustrating the first exemplary embodiment of the present invention with the first cooperative fastener elements.
Figure 8:
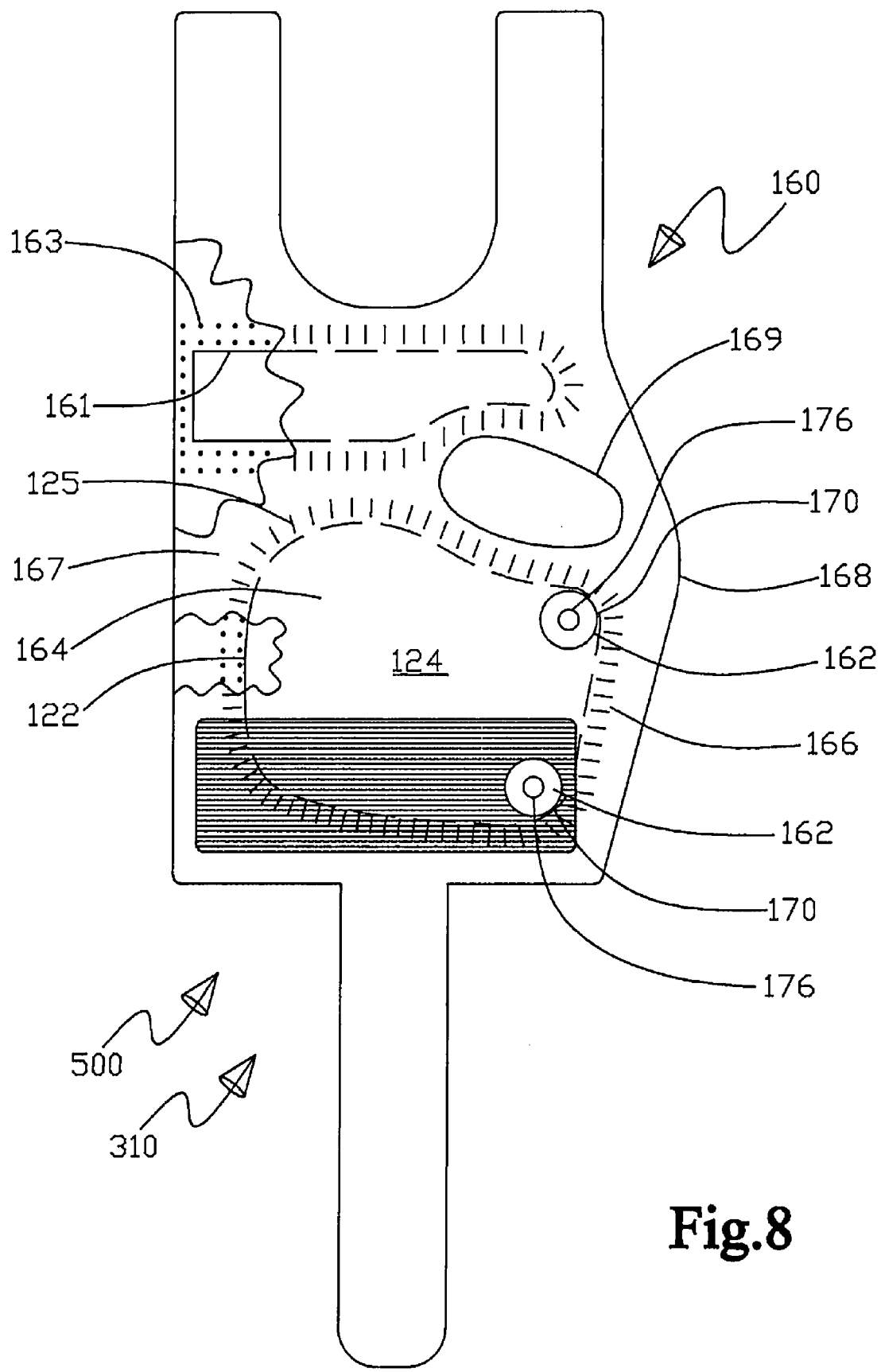
FIG. 8 is a plan or flat view, similar to FIG. 4, however, showing the first cooperative fastener elements of the first embodiment of the present invention that is located on the glove.

Continuing, in referring to FIGS. 7 and 8, the present invention is an archer's hand support structure apparatus 160, 260, 310, or 500 to help stabilize an archer's 81 hand 82 during string 46 or 70 draw and string 46 or 70 release of an archer's bow 30 or 50. The archer's hand support structure apparatus 160, 260, 310, or 500 includes a band 164 of flexible material adapted to encase the archer's hand 82, the band 164 having a first edge portion 166 extending adjacent to an archer's distal hand portion 110 and a second edge portion 167 extending adjacent to an archer's proximal hand portion 112. The band 164 also includes an aperture 169 therethrough disposed substantially adjacent to the first edge portion 166 for receiving a thumb 83 of the archer's 81 hand. Further, included is a stiffener 161 positioned adjacent to the band 164, the stiffener 161 also extending lengthwise substantially from the band first edge portion 166 to the band second edge portion 167. The band 164 also including a means 170 for selectively removably engaging the band 164 from the archer's bow 30 or 50. The band 164 is preferably constructed of a synthetic weather proof fabric that may or may not have some degree of rigidity itself, or any other material that has a functional use in wearing around an archer's 81 hand 82 in various weather conditions.

Further, on the archer's hand support 160, 260, 310, or 500 the stiffener 161 can be a malleable material disposed within a pocket 163 in the band 164 of flexible material. The stiffener 161 is preferably a rigid plastic or composite material; alternatively the stiffener 161 can be constructed of a corrosion resistant steel or any other fairly rigid and weather proof material. Continuing, on the stiffener 161, wherein the archer's hand 82 has a lengthwise axis 114 that is substantially perpendicular to a longwise axis 116 of the bow 30 or 50 and with the stiffener 161 preferably sized and configured to have a higher stiffness parallel 118 to the lengthwise axis 114 than to the longwise axis 116 having a lower stiffness 120, in referring to FIGS. 1, 6, 7, and 19.

With reference to FIGS. 6-10, a first exemplary embodiment 160 of the present invention is illustrated in conjunction with the handle 52 of a compound bow, however a conventional bow apparatus 30 would also be acceptable as it should be understood, though, that the structures described herein could be used with other bow handles, such as handle 32, and the like.

Looking first at FIG. 7, in archer's glove 160 is depicted a mounted state on the archer's hand 82. Glove 160 is illustrated in an unfolded condition, from the exterior side, in FIG. 8. Since the structure of archers glove 160 is substantially the same as that described with respect to the prior art glove 80, a detailed description of the structure will not be repeated. Rather, as illustrated in FIGS. 7 and 8, archer's glove 160 mounts a means 170 for removably engaging as a pair of glove first fastening elements 162 on a main body panel band 164 of glove 160. Glove fastening elements 162 are mounted in a first edge portion 166 adjacent to edge 168 with fastening elements 162 being spaced apart from one another a distance slightly less than the longitudinal length of handle 52. Similarly, with respect to FIG. 6, cooperative handle second fastening elements 172 are mounted in handle 52 the same distance apart as the spacing of the first fastening elements 162.

Figure 9:
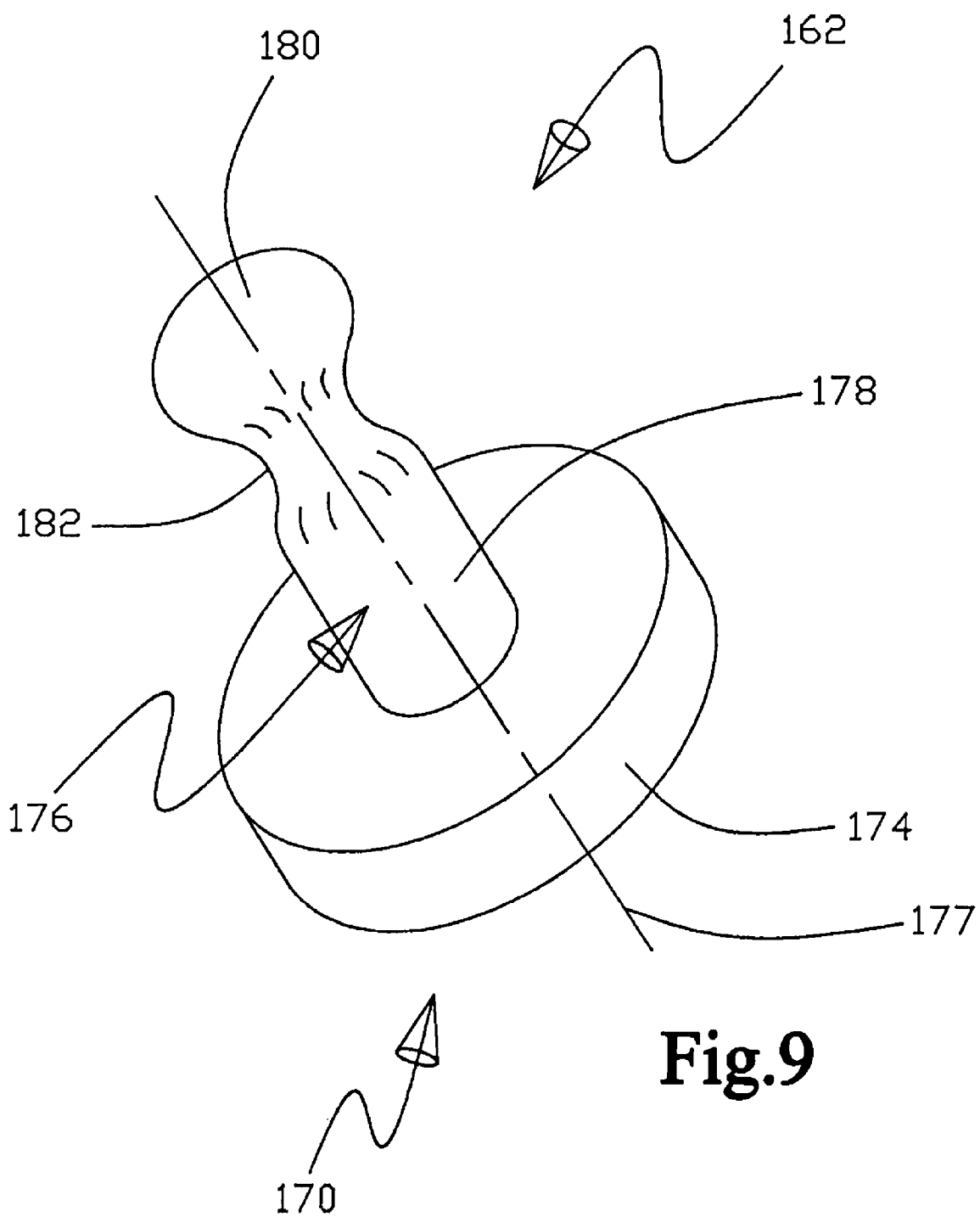
FIG. 9 is a perspective view of a first cooperative glove fastener element according to the first exemplary embodiment of the present invention.
Figure 10:
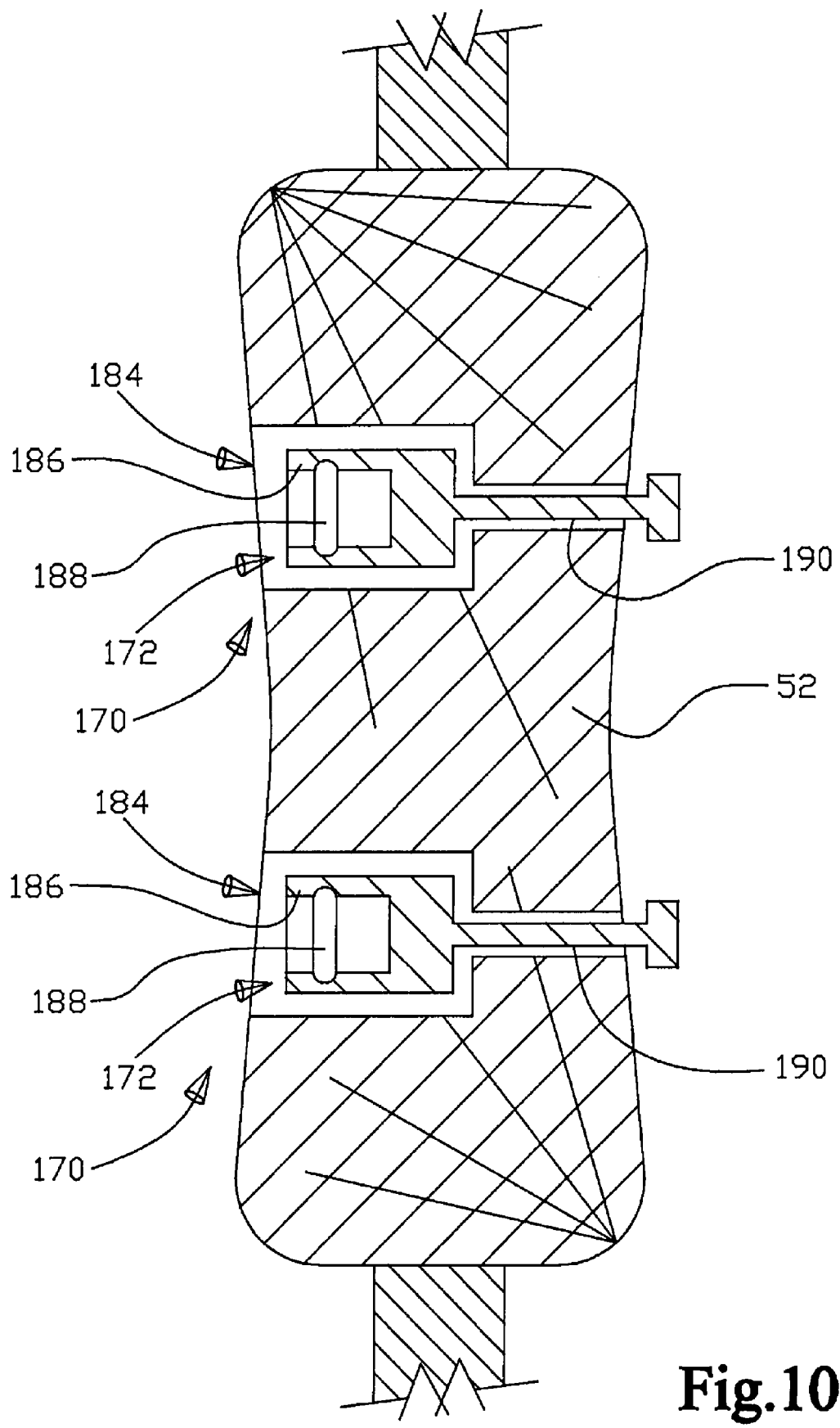
FIG. 10 is cross section 10-10 from FIG. 6 showing an end view in partial cross-section displaying the second cooperative fastener elements of the first exemplary embodiment of the present invention that is mounted relative to the bow handle.
Figure 11:
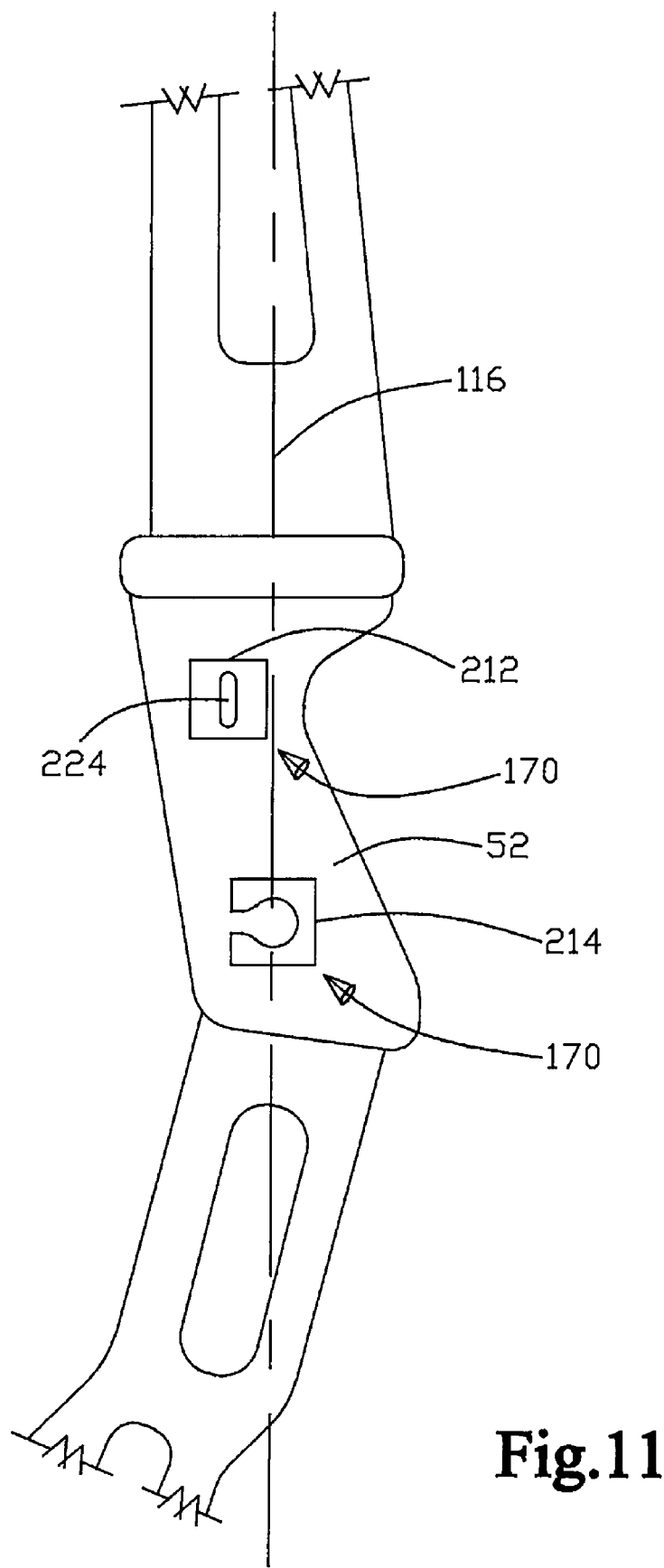
FIG. 11 is a side view in elevation showing the bow handle of FIG. 2 with fourth cooperative fastener elements according to a second exemplary embodiment of the present invention.

As is illustrated in FIG. 9, glove first fastening elements 162 are in the form of male members having a support base 174 from which a male prong 176 projects along a central longitudinal axis 177. Prong 176 includes a shaft 178 having a protruding head 180 at a free end thereof with head 180 and shaft 178 being joined by a reduced diameter neck 182. Cooperative second fastening element 172 is illustrated mounted in bore 184 of handle 52. Second cooperative fastening elements 172 include a female base 186 receptacle that is sized to receive prong 176 in close-fitted mated engagement. A detent 188 is provided to engage neck 182 on prong 176 to resiliently lock or removably engage prong 176 and female base 186 together so that glove 160 is secured to handle 52. A pull rod 190 is provided to selectively release detents 188 so that prongs 176 may be withdrawn from female base 186.

A second exemplary embodiment of the present invention 260 is illustrated in FIGS. 11-17. Again, this embodiment is similar to that described with respect to FIGS. 6-10 and is described with respect to handle 52 of a compound bow; again a convention bow 30 could also be used. In these Figures, it may be seen that handle 52 of the compound bow is provided with cooperative handle fastening elements of two different types. Here, as an alternative means 170 for removably engaging a third fastening element 212 is secured at the upper location on handle 52 while a fourth fastening element 214 is secured at the lower portion of handle 52.

Figure 13:
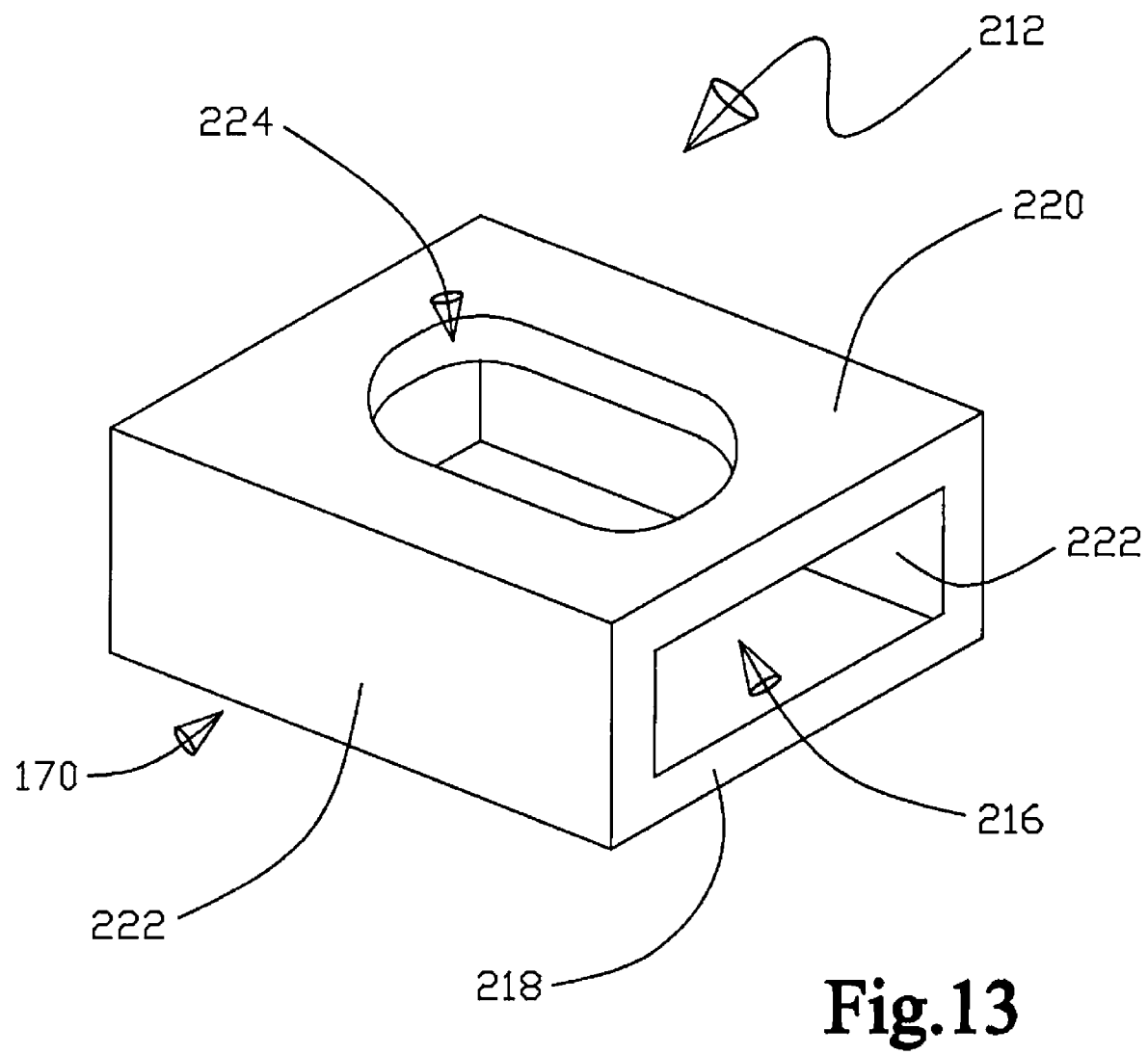
FIG. 13 is a perspective view of a third cooperative bow fastening element according to the second exemplary embodiment of the present invention.

Third fastening element 212 is illustrated in FIG. 13 where it may be seen that the third fastening element 212 has an interior 216 formed between a lower wall 218 and a parallel top wall to 220 and sidewalls 222. An elongated oval opening 224 is formed through top wall 220 and it may be appreciated that opening 224 as a longitudinal length that is greater than its width.

Figure 15:
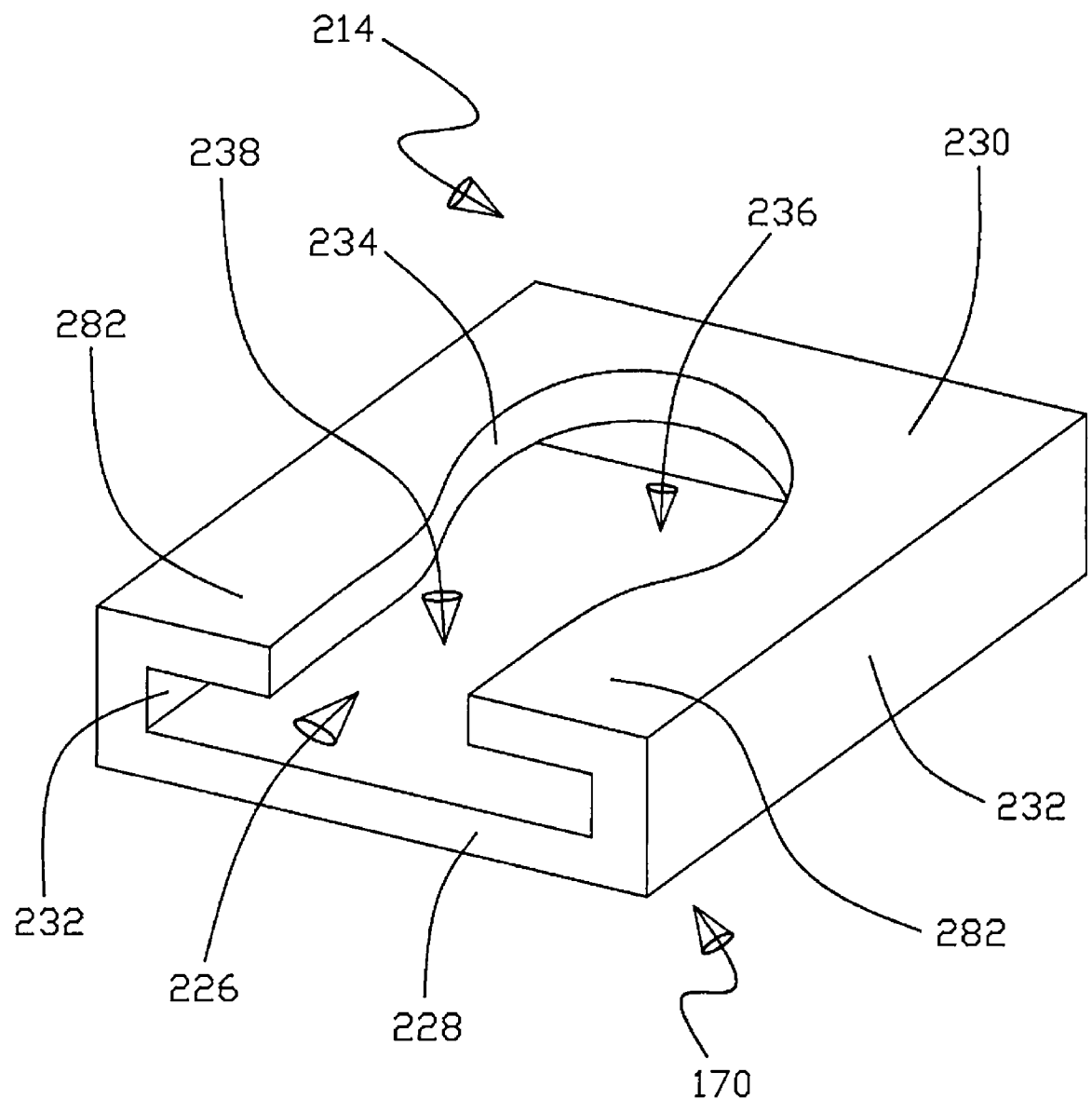
FIG. 15 is a perspective view showing a fourth cooperative glove fastening element according to the second exemplary embodiment of the present invention.

Fourth fastening element 214 is illustrated in FIG. 15 and has an interior 226 formed by a lower wall 228, a top wall 230 and a pair of sidewalls 232. A keyhole-shaped opening 234 is formed in top wall 230 and includes a wider region 236 and a narrower mouth region 238.

Figure 12:
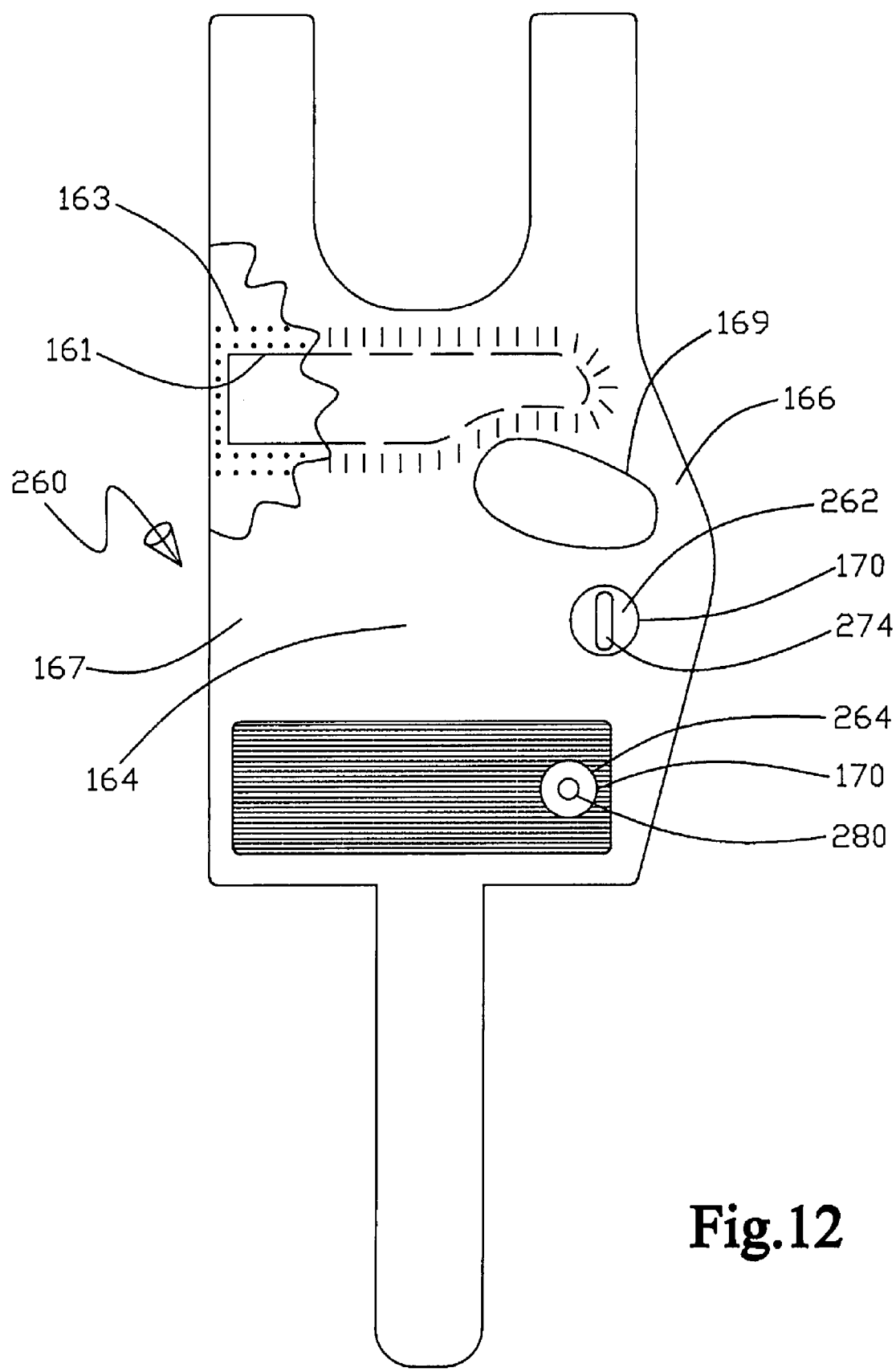
FIG. 12 is a plan view of the archer's glove, similar to FIGS. 4 and 8, illustrating the fifth and sixth cooperative glove fastener elements according to the second exemplary embodiment of the present invention.
Figure 14:
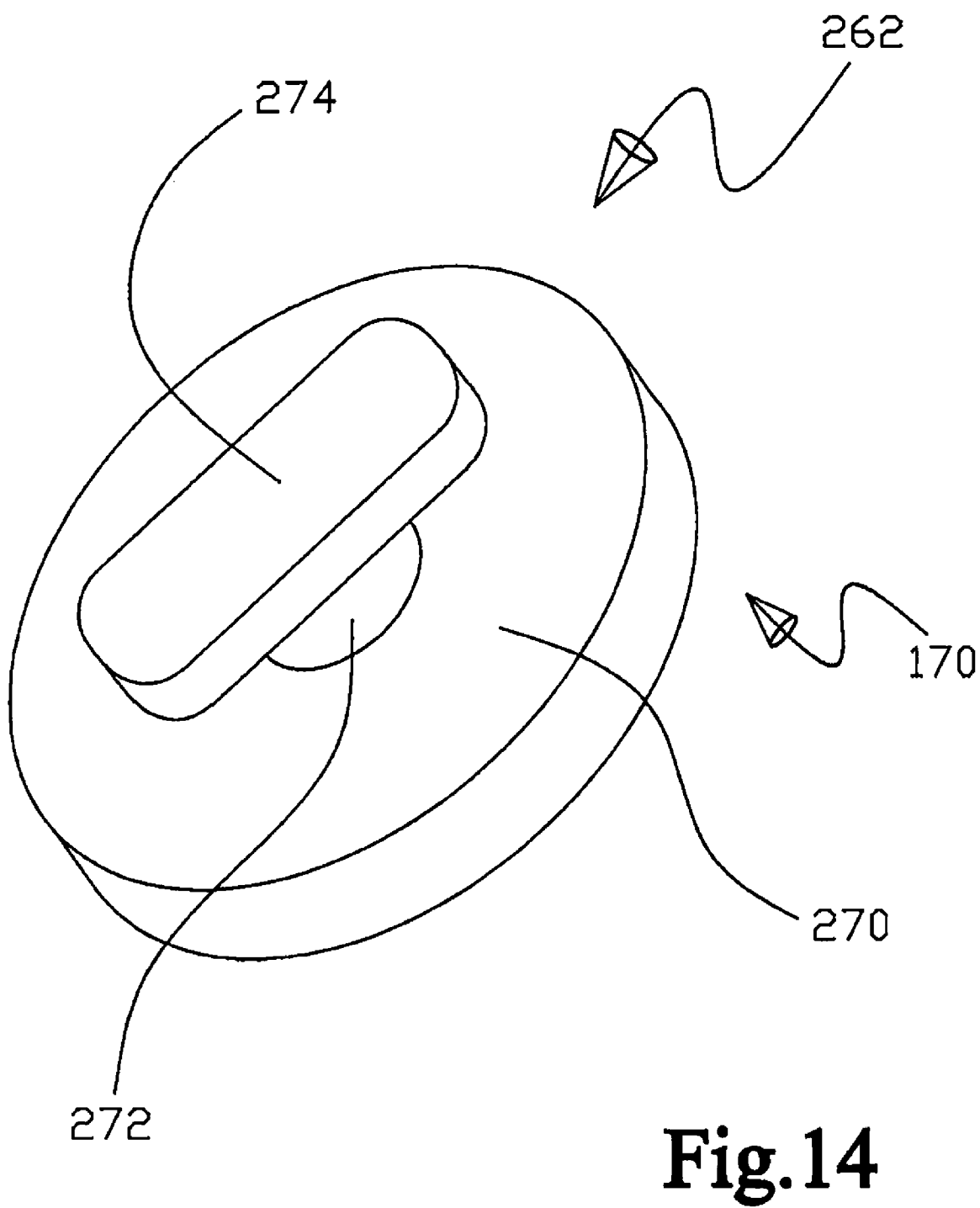
FIG. 14 is a perspective view of a fifth cooperative glove fastening element that is adapted for use with the third bow fastening element of FIG. 13 according to the second exemplary embodiment of the present invention.
Figure 17:
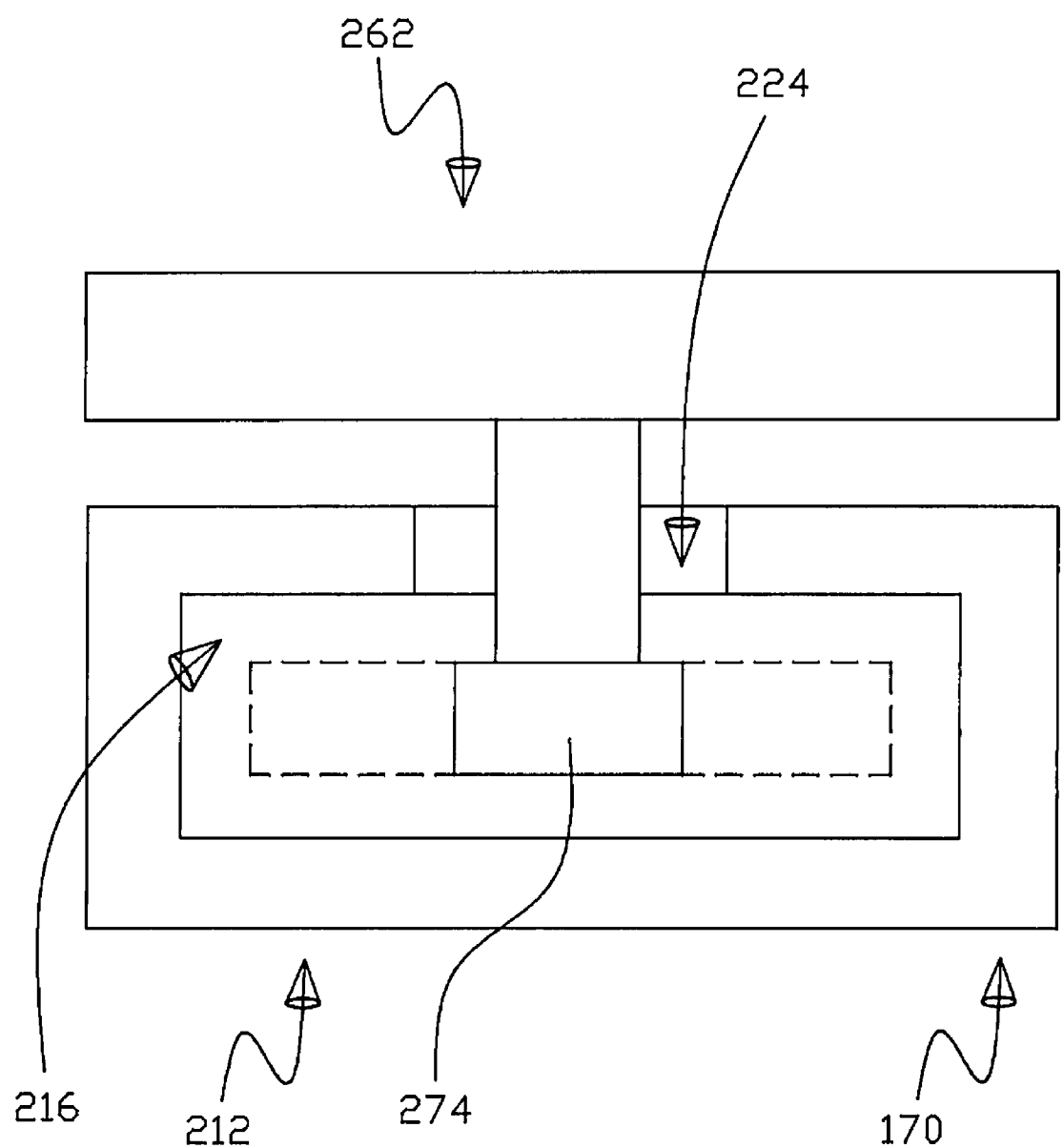
FIG. 17 is an end view in elevation showing engagement of the third cooperative fastening element of FIG. 13 and the fifth cooperative fastening element of FIG. 14.

With reference now to FIG. 12, it may be seen that an alternative embodiment of archer's glove 260 supports a cooperative glove fifth fastening element 262 and sixth fastening element 264. Glove fifth fastening element 262 is adapted to cooperatively engage the handle third fastening element 212, and is illustrated best in FIG. 17. With reference to FIGS. 14 and 17, it may be seen that the fifth fastening element 262 includes a base 270 that supports a shaft 272 that has an elongated oval head 274 and upper end thereof. Head 274 is sized to pass through opening 224 when properly registered therewith.

Figure 16:
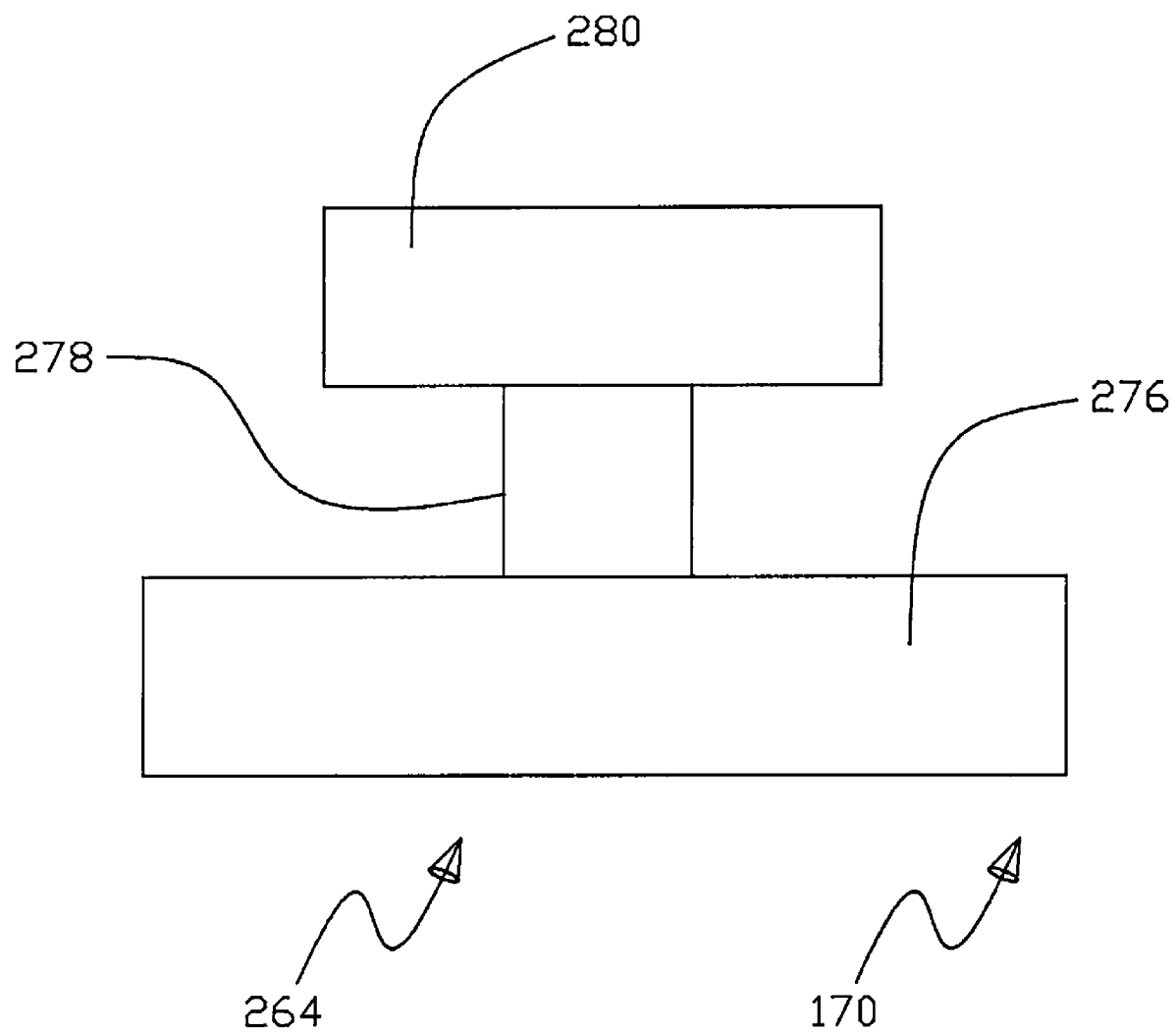
FIG. 16 is a side view in elevation illustrating a sixth cooperative glove fastening element according to the second exemplary embodiment of the present invention.

Glove sixth fastening element 264 is best illustrated in FIG. 16 and includes a base 276 that supports a shaft 278, and a circular head 280 is located to the upper end of shaft 278. Shaft 278 is sized to pass through mouth region 238 of handle fourth fastening element 214, but head 280 is sufficiently large so that it will not pass through region 236. Region 236 is slightly wider, though, than mouth region 238 so that opposed nubs 282 "snap fit" around shaft 278 so that fourth fastening element 214 removably mechanically engages sixth fastening element 264.

Fifth fastening element 262 is orientated so that head 274 will pass through opening 224 when the archer's hand 82 is longitudinally aligned with handle 52. This engagement is illustrated in solid lines in FIG. 17. After inserting head 274 into interior 216, the archer's hand 82 may be rotated ninety degrees into a normal gripping state such that the archer's hand 82 can grasp handle 52. This rotation rotates head 274 ninety degrees to a position shown in dashed lines in FIG. 17 so that head 274 may not be withdrawn from interior 216. Similarly, this rotation engages fourth fastening element 214 and sixth fastening element 264 and a "snap fit" relationship described above.

Figure 18:
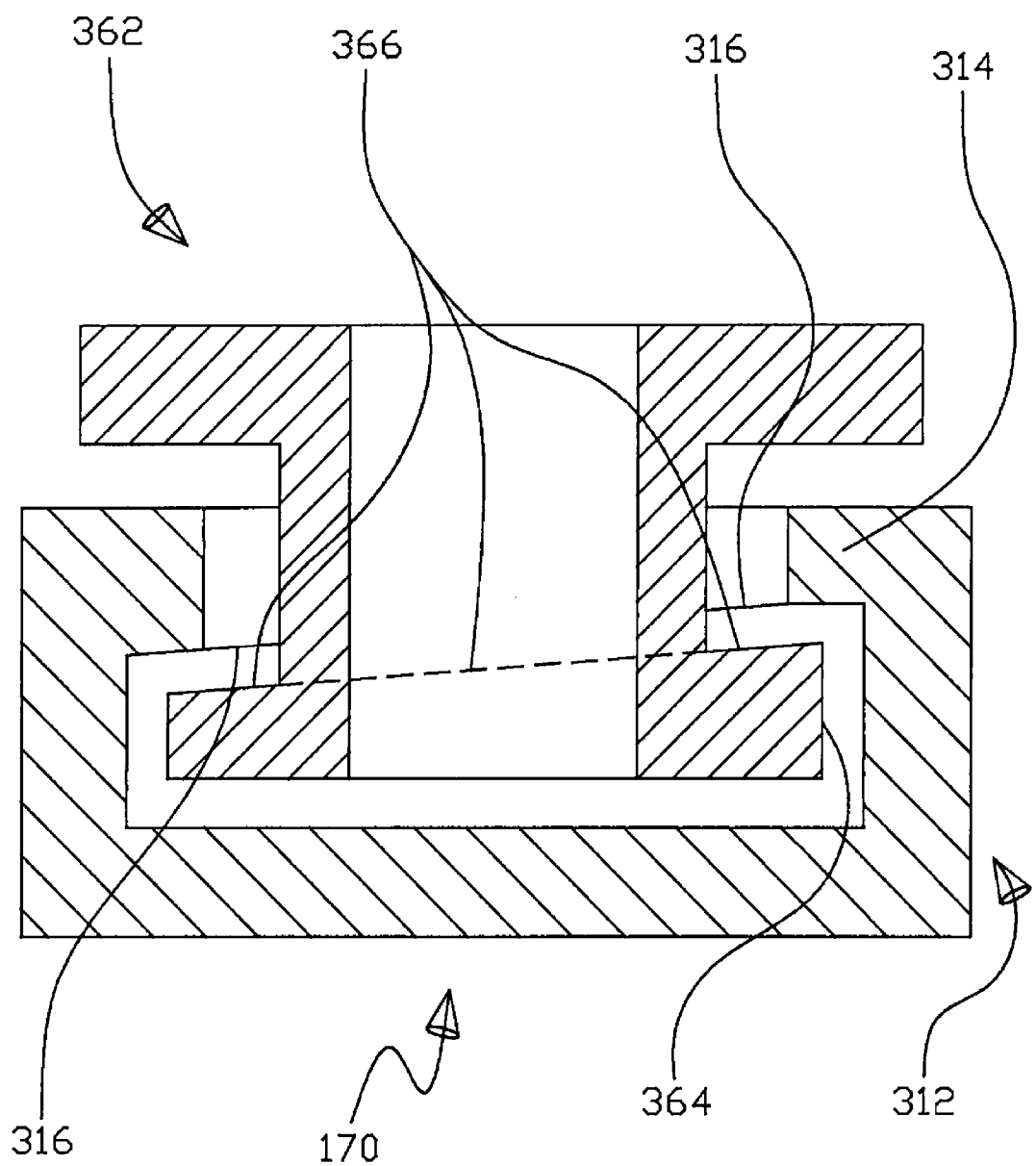
FIG. 18 is an end view in cross-section showing engagement of the third exemplary embodiment of the seventh and eighth cooperative fastening elements according to the present invention.

With reference now to FIG. 18, an alternate means 170 for removably engaging is a pair of cooperative fastening elements that could be used instead of the third fastening element 212 and fifth fastening element 262, is illustrated in FIG. 18. Here, seventh fastening element 312 includes a thread 314 that is provided with an interior cam surface 316. Eighth fastening element 362 is provided with a radially outwardly projecting thread 364 having a cam surface 366. Seventh fastening element 312 and eighth fastening element 362 are configured so that the 90-degree rotation of the archer's hand 82, described above, will engage the threads 314 and 364 so that cam surfaces 316 and 366 draw the seventh fastening element 312 and the eighth fastening element 362 tightly together. Counter-rotation of 90 degrees, however, will release the seventh fastening element 312 and the eighth fastening element 362.

An archer's hand support structure apparatus comprising a fourth embodiment 500 as best shown in FIGS. 7 and 8 to help stabilize the archer's hand 82 during string 46 and 70 draw and string 46 and 70 release of an archer's bow 30 or 50, includes a band 164 of flexible material adapted to encase the archer's hand 82, the band 164 having a first edge portion 166 extending adjacent to an archer's distal hand portion 110 and a second edge portion 167 extending adjacent to an archer's proximal hand portion 112. Note that in referring to FIGS. 7 and 8 for the fourth embodiment 500 that the first fastening elements 162 are removed from the band 164. The band 164 also includes an aperture 169 therethrough disposed substantially adjacent to the first edge portion 166 for receiving a thumb 83 of the archer's 81 hand 82. Further, included is a stiffener 161 positioned adjacent to the band 164, the stiffener 161 also extending lengthwise substantially from the band first edge portion 166 to the band second edge portion 167, with the optional preferred malleable materials of construction and the alternative higher and lower stiffness's 118 and 120 of the stiffener 161 optionally in a pocket 163 are all as previously described.

Figure 19:
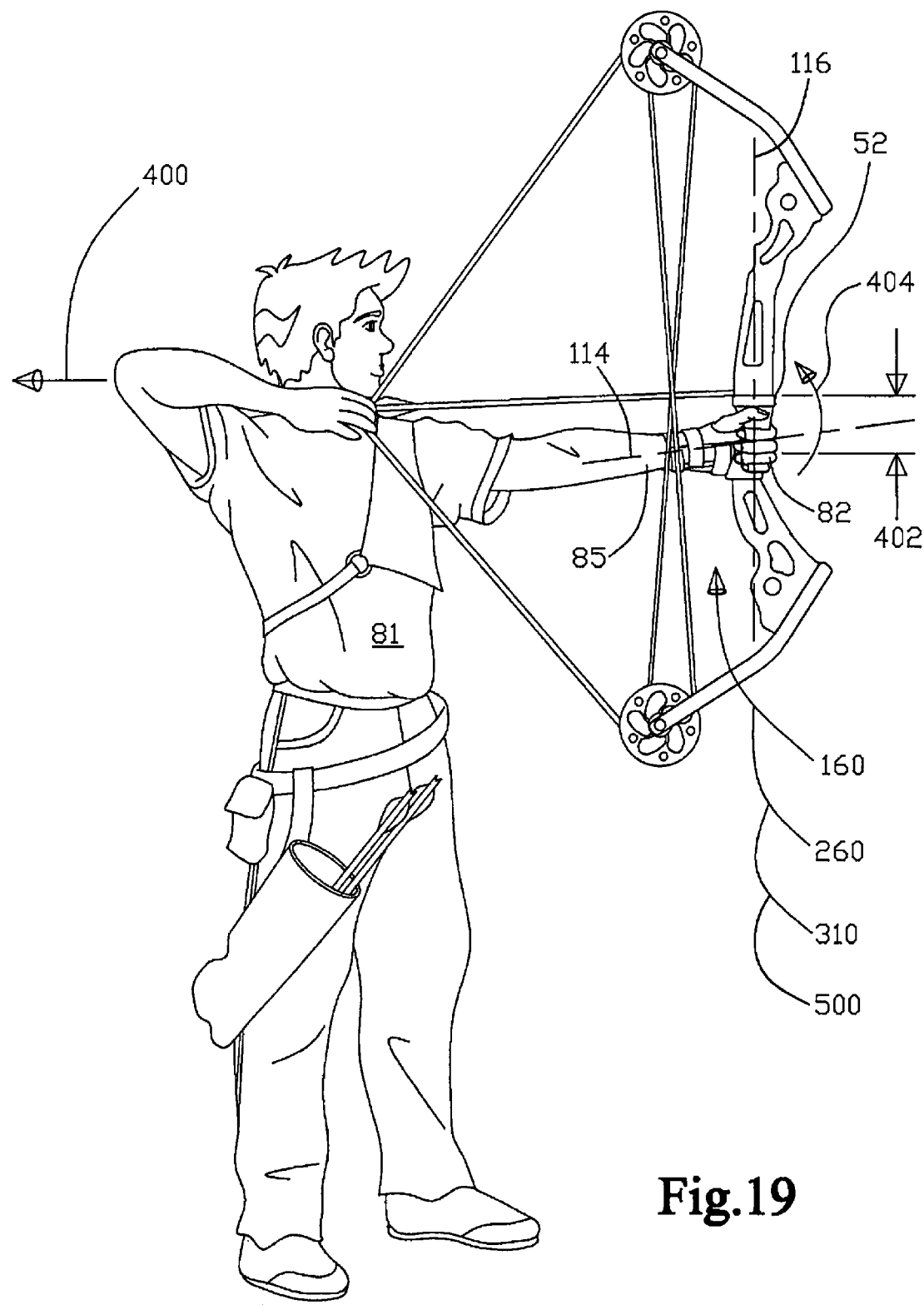
FIG. 19 is a side use view of the archer using a bow with the drawstring fully pulled, with the archer using the archer's glove apparatus.
Figure 20:
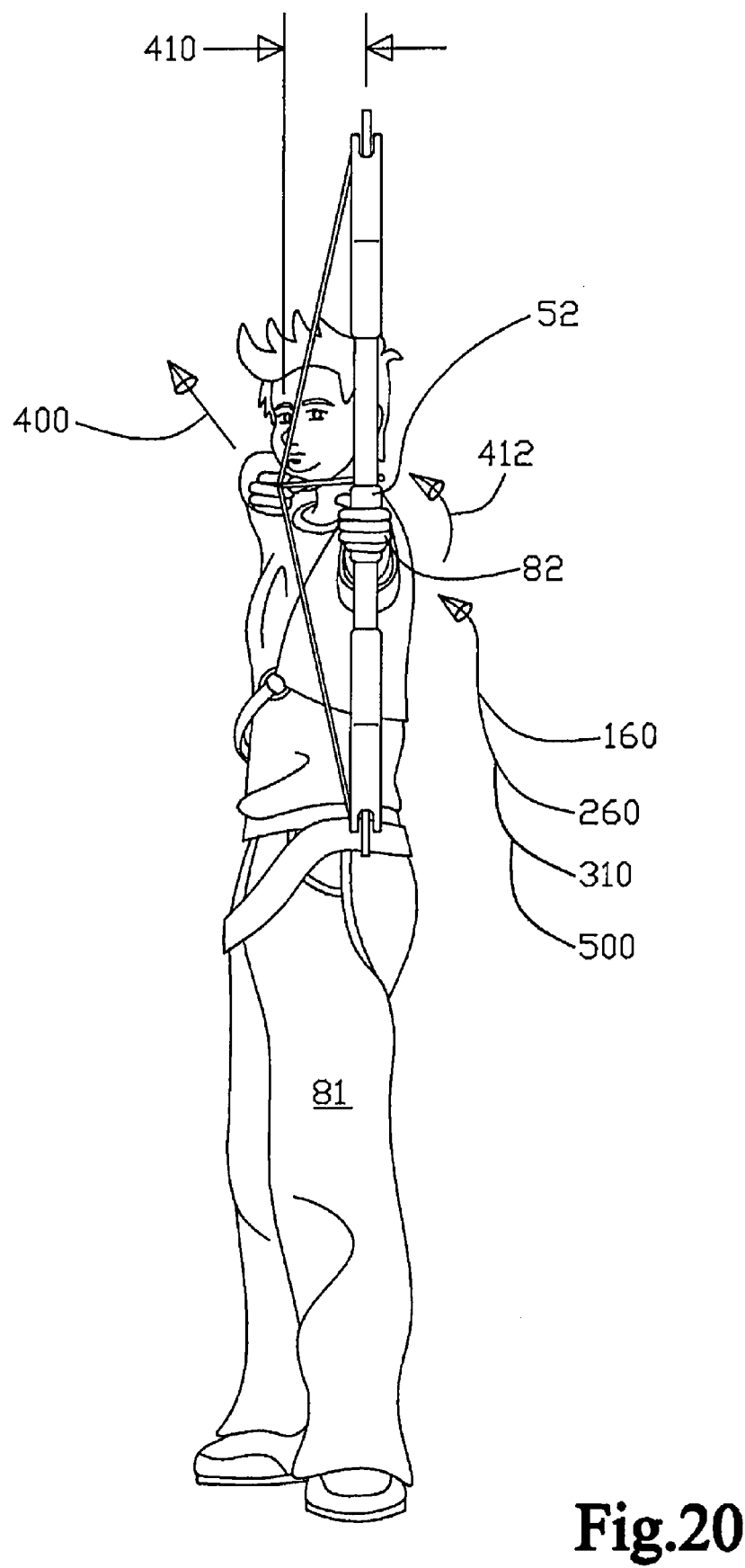
FIG. 20 is an end use view of the archer using a bow with the drawstring fully pulled, with the archer using the archer's glove apparatus.

Further included in the fourth embodiment 500 is a semi rigid member 122 positioned adjacent to the band to substantially cover a palm area 124 of the archer's hand 82, the member 122 is formed to substantially match in a nesting non engaging relationship the bow handle 32 or 52 shape that is adjacent to the archer's hand palm 124 of the bow 30 or 50 during use, to help prevent unwanted movement during string 46 or 70 draw and release by distributing a load, as shown by moments 404 and 412 from FIGS. 19 and 20 from the bow handle 32 or 52 to over a greater area of the archer's palm 124. Thus, the member 122 will preferably be a semi rigid material that can conform to the handle 32 or 52 shape while distributing the bow moments 404 and 412 to an area greater than the handle 32 or 52 would normally contact with the archer's palm 124. Note that the member 122 can also be disposed within a pocket 125 similar to stiffener 161. The member 122 materials of construction could include bendable deformable plastics, lead/tin alloys such as pewter, or any other material that is semi rigid and weather proof.

Method of Use

With primary reference to use FIGS. 19 and 20 for the archer's 81 hand 82 support structure apparatus 160, 260, 310, or 500 a method or use is given with reference to structural elements as previously given. The method of using an archer's hand support 160, 260, 310, or 500 to help prevent undesirable movement through moments 404 and 412 upon an archer's hand 82 during string 46 or 70 draw force 400 and subsequent release of the bow comprises the steps of; firstly providing the present invention in an archer's hand support structure apparatus 160, 260, 310, or 500 to help stabilize an archer's 81 hand 82 during string 46 or 70 draw and string 46 or 70 release of an archer's bow 30 or 50. The archer's hand support structure apparatus 160, 260, 310, or 500 includes a band 164 of flexible material adapted to encase the archer's hand 82, the band 164 having a first edge portion 166 extending adjacent to an archer's distal hand portion 110 and a second edge portion 167 extending adjacent to an archer's proximal hand portion 112.

The band 164 also includes an aperture 169 therethrough disposed substantially adjacent to the first edge portion 166 for receiving a thumb 83 of the archer's 81 hand. Further, included is a stiffener 161 positioned adjacent to the band 164, the stiffener 161 also extending lengthwise substantially from the band first edge portion 166 to the band second edge portion 167. The band 164 also including a means 170 for selectively removably engaging the band 164 from the archer's bow 30 or 50 or alternatively in the fourth embodiment 500 is a semi rigid member 122 positioned adjacent to the band to substantially cover a palm area 124 of the archer's hand 82, the member 122 is formed to substantially match in a nesting non engaging relationship the bow handle 32 or 52 shape that is adjacent to the archer's hand palm 124 of the bow 30 or 50 during use.

A next step is in placing the band 164 of flexible material to encase the archer's hand 82 with the archer's thumb 83 protruding through the aperture 169, as best shown in FIGS. 7 and 19, further a step of positioning the means 170 for removably engaging proximate to the bow 30 or 50 to engage the band 164 to the bow 30 or 50 or more particularly the bow handle 32 or 52. Next, a step of grasping the bow 30 or 50 with the archer's hand 82 that is encased with the band 164, and a further step of drawing through force 400 and releasing the bow string 46 and 70. With the goal of the archer's hand support 160, 260, 310, or 500, looking in particular at FIGS. 19 and 20, being to help prevent the reduction in bow shooting accuracy from the inherent effects of the moment arm offsets 402 and 410 that come from the centroid of the pulling force 400 being at the intersection of the arrow and the bow string 46 and 70 thus resulting in the moment arm offsets 402 and 410 that are the offset distances from the centroid of the pulling force 400 and the archer's hand 82 grip on the bow handle 32 and 52. Due to the nature of typical bow 30 or 50 design, these offsets 402 and 410 being in conjunction with force 400 result in moments 404 and 412 that cause an unsymmetric load on the archer's hand 82, wherein the archer's hand 82 must compensate for this un-symmetric load in an opposing direction to the moments 404 and 412, wherein the present invention assists in the archer 81 in this un-symmetric load compensation by diffusing the load compensation over a greater area of the archer's 81 hand 82 and potentially the archer's arm 85 resulting in more archer's hand 82 stability and less fatigue upon the archer's hand 82.

Optionally, the positioning step could further include initiating a relative rotation between the band 164 and the bow 30 or 50 that is operational to engage the band 164 to the bow 30 or 50, as previously described for the second embodiment 260 and the third embodiment 310. Further, another optional step could be in the positioning step relative rotation continuing until rotational frictional force precludes additional relative rotation, wherein the band 164 and the bow 30 or 50 are engaged, also as previously described for the second embodiment 260 and the third embodiment 310. Again further optionally, the providing step could substitute the nesting member 122 that is adjacent to the band 164 for the means 170 for removably engaging the band 164 from the archer's bow 30 or 50 and wherein the positioning and grasping steps are combined for a step of forming the nesting member 122 to be adjacent to the bow handle 32 or 52, as previously described for the fourth embodiment 500.

Accordingly, the present invention has been described with some degree of particularity directed to the exemplary embodiment of the present invention. It should be appreciated, though, that the modifications or changes may be made to the exemplary embodiment of the present invention without departing from the inventive concepts contained herein.

The invention claimed is:

1. An archer's hand support structure apparatus to help stabilize an archer's hand during string draw and string release of an archer's bow, and otherwise secure the archer's bow to said archer's hand support structure without manually grasping, when the archer is carrying the bow without string draw and release, comprising:

(a) a band of flexible material adapted to encase the archer's hand, said band having a first edge portion extending adjacent to an archer's distal hand portion and a second edge portion extending adjacent to an archer's proximal hand portion, said band also includes an aperture therethrough disposed substantially adjacent to said first edge portion for receiving a thumb of the archer's hand;

(b) a stiffener positioned adjacent to said band, said stiffener also extending lengthwise substantially from said band first edge portion to said band second edge portion; and (c) a third fastening element affixed to a bow handle, said third fastening element having an elongated oval opening having a longitudinal length greater than its width, said elongated oval being disposed therethrough a third fastening element top wall into a third interior that is formed between a third fastening element lower wall that is parallel to said third fastening element to wall and a third fastening element pair of sidewalls, further a fourth fastening element affixed to the bow handle, said fourth fastening element having a keyhole opening that is formed into a fourth fastening element top wall, with said keyhole opening being shaped with a wider region and a narrower mouth therethrough said fourth fastening element top wall to a fourth interior that is formed from said fourth fastening element top wall, a fourth fastening element lower wall, and a pair of fourth fastening element sidewalls, further a fifth fastening element with an elongated oval head forming a "T" section that is cooperatively received therethrough by said third fastening element top wall and into said third interior, said fifth fastening element is securely engaged by rotating said fifth fastening element relative to said third fastening element, further included is a sixth fastening element having a circular head on a smaller diameter shaft, wherein said smaller diameter shaft removably engages said fourth fastening element narrower mouth, and said circular head is larger than said wider region, wherein said fifth and sixth fastening elements are affixed to said band, wherein operationally after said receiving of said fifth fastening element into said third fastening element to securely engage said archer's hand support to the archer's bow when an archer's arm lengthwise axis is not perpendicular to a bow longwise axis and said fourth and sixth fastening elements are not engaged allowing the bow to be carried without an archer's hand grasp grip on the bow handle with the archer not completing the string draw and release, further operationally when said fifth and third fastening elements are securely engaged in conjunction with said fourth and sixth fastening elements being engaged the archer's hand is stabilized during the string draw and string release of the archer's bow.

2. An archer's hand support according to claim 1, wherein said stiffener is a malleable material disposed within a pocket in said band of flexible material.

3. An archer's hand support structure apparatus to help stabilize an archer's hand during string draw and string release of an archer's bow, and otherwise secure the archer's bow to said archer's hand support structure without manually grasping, when the archer is carrying the bow without string draw and release, comprising:

(a) a band of flexible material adapted to encase the archer's hand, said band having a first edge portion extending adjacent to an archer's distal hand portion and a second edge portion extending adjacent to an archer's proximal hand portion, said band also includes an aperture therethrough disposed substantially adjacent to said first edge portion for receiving a thumb of the archer's hand;

(b) a stiffener positioned adjacent to said band, said stiffener also extending lengthwise substantially from said band first edge portion to said band second edge portion; and (c) a seventh fastening element with a thread and an interior cam surface, wherein said seventh fastening element is affixed to a bow handle and an eighth fastening element with a radially outward projecting thread and a cam surface, with said eighth fastening element affixed to said band, said eighth fastening element removably engages said seventh fastening element by way of a relative rotation of about ninety (90) degrees between said seventh and eighth fastening elements that draws said seventh and eighth fastening elements substantially tightly together through said threads and cam surfaces frictionally engaging one another, being operational for the archer's string draw and release of the bow, wherein reverse relative rotation of about ninety (90) degrees between said seventh and eighth fastening elements disengages said seventh and eighth fastening elements, wherein operationally a relative rotation of less than ninety (90) degrees as between said seventh and eighth fastening elements allows for a loose engagement as between said seventh and eighth fastening elements being operational to engage said archers hand support to the archers bow when an archers arm lengthwise axis is not perpendicular to a bow longwise axis allowing the bow to be carried without an archers hand grip on the bow handle, with the archer not completing the string draw and release.

* * * * *